(12) United States Patent
Xu et al.

(10) Patent No.: US 10,303,847 B2
(45) Date of Patent: May 28, 2019

(54) SINGLE MOLECULE IDENTIFICATION USING INTENSITY TIME SEQUENCING, LINE CHARTING AND RUN-LENGTH CODING

(71) Applicant: DIRECT GENOMICS CO., LTD., Shenzhen (CN)

(72) Inventors: Weibin Xu, Shenzhen (CN); Huan Jin, Shenzhen (CN); Qin Yan, Shenzhen (CN); Zefei Jiang, Shenzhen (CN); Zhiliang Zhou, Shenzhen (CN)

(73) Assignee: Direct Genomics Co., Ltd., Shenzhen (CN)

( * ) Notice: Subject to any disclaimer, the term of this patent is extended or adjusted under 35 U.S.C. 154(b) by 0 days.

(21) Appl. No.: 15/824,108

(22) Filed: Nov. 28, 2017

(65) Prior Publication Data
US 2018/0165409 A1    Jun. 14, 2018

(30) Foreign Application Priority Data

Dec. 9, 2016 (CN) .......................... 2016 1 1129604
Jul. 24, 2017 (CN) .......................... 2017 1 0607586

(51) Int. Cl.
G06T 7/00 (2017.01)
G06F 19/16 (2011.01)
G06F 19/22 (2011.01)

(52) U.S. Cl.
CPC .............. *G06F 19/16* (2013.01); *G06F 19/22* (2013.01); *G06T 7/0012* (2013.01)

(58) Field of Classification Search
None
See application file for complete search history.

(56) References Cited

FOREIGN PATENT DOCUMENTS

| CN | 105243677 A | 1/2016 |
|---|---|---|
| CN | 105303540 A | 2/2016 |
| CN | 105303551 A | 2/2016 |

OTHER PUBLICATIONS

Wikipedia on Erosion in morphology at https://en.wikipedia.org/wiki/Erosion_(morphology) (2018).*
Bin et al., "Fast Fourier-Domain Localization Algorithm of Single Molecule with Nanometer Resolution for Super-Resolution Fluorescence Imaging," *Acta Optica Sinica* 32(2): 0218001-2-0218001-6, 2012. (English Abstract Only).
Wei et al., "Single molecule fluorescence fluctuations of the cyanine dyes linked covalently to DNA," *Sci. China Ser. B-Chem* 52(8): 1148-1153, 2009.
Gao et al., "Single molecule targeted sequencing for cancer gene mutation detection," *Scientific Reports* 6(26110):1-11 (May 19, 2016).
Rolfe et al., "Automated multidimensional single molecule fluorescence microscopy feature detection and tracking," *Eur Biophys J* 40:1167-1186 (2011).
McGuire et al., "Automating Single Subunit Counting of Membrane Proteins in Mammalian Cells," *Journal of Biological Chemistry* 287(43):35912-35921 (Oct. 19, 2012).
Yuan et al., "Analysis of the Steps in Single-Molecule Photobleaching Traces by Using the Hidden Markov Model and Maximum-Likelihood Clustering," *Chem. Asian J.* 9:23-3-2308 (2014).

* cited by examiner

*Primary Examiner* — G Steven Vanni
(74) *Attorney, Agent, or Firm* — Seed IP Law Group LLP

(57) ABSTRACT

A method and a device for identifying a single molecule, a method and a device for counting a single molecule and a system for processing a single molecule are provided. The method for identifying the single molecule includes inputting time sequence of an intensity of an spot; forming a line chart of time and intensity of the spot according to the time sequence, wherein the line chart consists of a plurality of line segments; dividing the line chart into a plurality of grids in an array, counting the number of the line segments and/or ends of the line segments in each grid; subjecting the divided line chart to a line erosion according to numbers corresponding to the grids to transform the divided line chart to a simplified image; subjecting the simplified image to run-length coding to indicate connected domains; calculating an area of each connected domain and determining that the connected domain corresponds to a single molecule if the area of the connected domain is greater than a first predetermined threshold. According to the method for identifying the single molecule, the line chart of the time sequence of the intensity of the spot is processed to transform into the image, which results in a quick identification for the single molecule and a high accuracy of the identification.

20 Claims, 28 Drawing Sheets

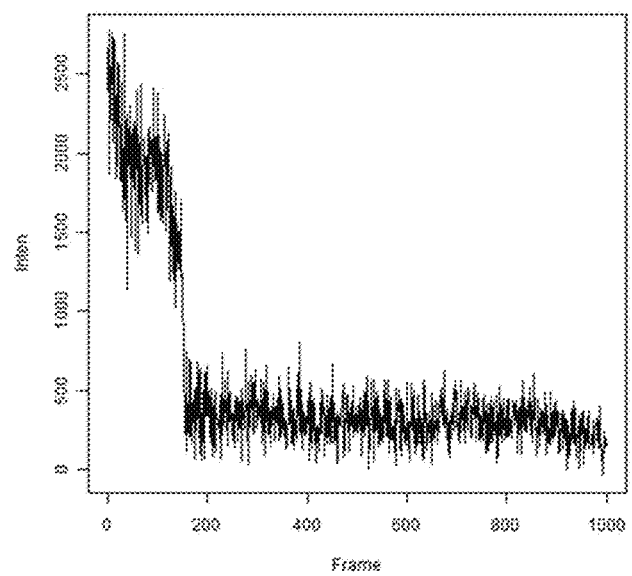
FIG. 14
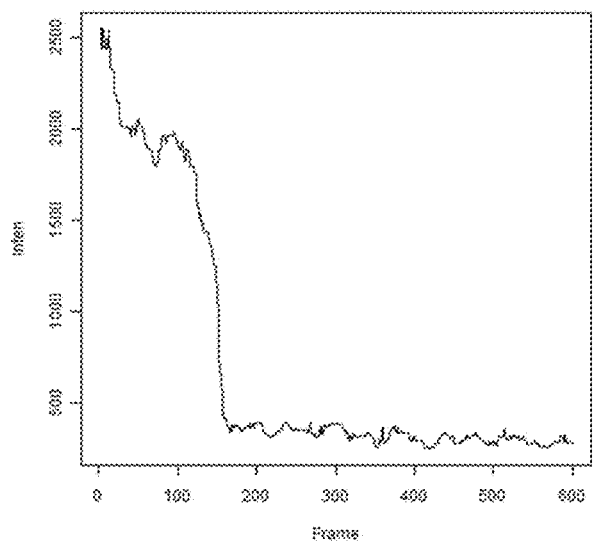
FIG. 15
| 1 | 1 | 1 | 0 |
|---|---|---|---|
| 0 | 2 | 1 | 0 |
| 0 | 0 | 0 | 0 |
| 0 | 0 | 0 | 0 |
FIG. 16

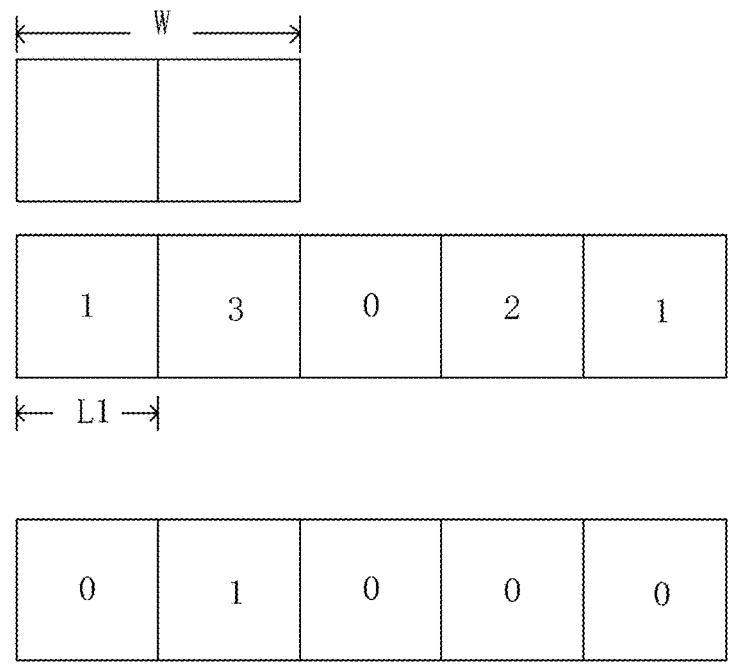
FIG. 19
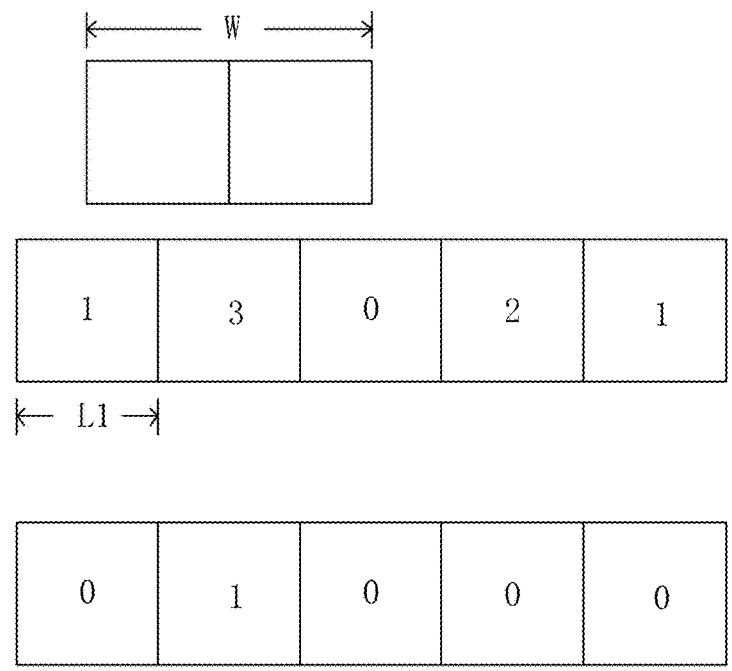
FIG. 20
| 1 | 1 | 1 |
|---|---|---|
| 1 | 1 | 1 |
| 1 | 1 | 1 |
FIG. 21

| 9 | 9 | 9 | 9 | 0 | 0 | 0 | 0 |
|---|---|---|---|---|---|---|---|
| 9 | 9 | 9 | 0 | 0 | 0 | 0 | 0 |
| 0 | 9 | 9 | 0 | 7 | 7 | 0 | 0 |
| 0 | 0 | 0 | 0 | 7 | 7 | 0 | 0 |
| 0 | 0 | 0 | 0 | 7 | 7 | 7 | 7 |
| 0 | 0 | 0 | 0 | 7 | 7 | 7 | 7 |
| 0 | 0 | 0 | 0 | 7 | 7 | 7 | 7 |
| 0 | 0 | 0 | 0 | 7 | 7 | 7 | 7 |

FIG. 22

SINGLE MOLECULE IDENTIFICATION USING INTENSITY TIME SEQUENCING, LINE CHARTING AND RUN-LENGTH CODING

CROSS REFERENCE OF RELATED APPLICATIONS

This application claims the benefit under 35 U.S.C. 119 (a)-(d) to Chinese Application No. 201611129604.1, filed Dec. 9, 2016, and Chinese Application No. 201710607586.1, filed Jul. 24, 2017, which applications are hereby incorporated by reference in their entireties.

FIELD

The present disclosure relates to a field of gene sequencing technology, and more particularly relates to a method and a device for identifying a single molecule, a method and a device for counting a single molecule and a system for processing a single molecule.

BACKGROUND

In the related art, the third generation sequencing technology is a single molecule sequencing technology based on imaging optical detections. Moreover, the single molecule sequencing technology is a technology for identifying base groups according to optical signals and electrical signals. Specifically, a base group is identified by fluorescence which is a light intensity emitted from an excited state to a ground state at a specific power laser irradiation. However, due to different fluorophores illumine for different time durations and have different light intensities, as well as the presence of background noise, it is possible to cause errors for identification of the single molecules. At the same time, an effective number of single molecules may be reduced by uneven distribution of DNA chain and agglomeration of base groups.

The existing methods rely mainly on the human eye to identify and count single molecules on a collected fluorescence image, but these methods cost a lot of labor and time. With reference to phonetic identification, if a method according to HMM (Hidden Markov Model) and machine study is used, a lot of training is required and operating efficiency is not high.

SUMMARY

Embodiments of the present disclosure seek to solve at least one of the problems existing in the related art to at least some extent. Accordingly, embodiments of the present disclosure provide a method and a device for identifying a single molecule and a method and a device for counting a single molecule.

A method for identifying a single molecule is provided according to embodiments of the present disclosure. The method includes inputting time sequence of an intensity of an spot; forming a line chart of time and intensity of the spot according to the time sequence, in which the line chart consists of a plurality of line segments; dividing the line chart into a plurality of grids in an array, counting the number of the line segments and/or ends of the line segments in each grid; subjecting the divided line chart to a line erosion according to numbers corresponding to the grids to transform the divided line chart to a simplified image; subjecting the simplified image to run-length coding to indicate connected domains; calculating an area of each connected domain and determining that the connected domain corresponds to a single molecule if the area of the connected domain is greater than a first predetermined threshold. According to the method for identifying the single molecule, the line chart of the time sequence of the intensity of the spot is processed to transform into the image, which results in a quick identification for the single molecule and a high accuracy of the identification.

A method for counting a single molecule is provided according to embodiments of the present disclosure. The method includes: inputting time sequence of an intensity of an spot; forming a line chart of time and intensity of the spot according to the time sequence, in which the line chart consists of a plurality of line segments; dividing the line chart into a plurality of grids in an array, counting the number of the line segments and/or ends of the line segments in each grid; subjecting the divided line chart to a line erosion according to numbers corresponding to the grids to transform the divided line chart to a simplified image; subjecting the simplified image to run-length coding to indicate connected domains; calculating an area of each connected domain, and determining that the connected domain corresponds to a single molecule if the area of the connected domain is greater than a first predetermined threshold; obtaining a first number of the single molecules by calculation. According to the method for counting the single molecule, the line chart of the time sequence of the intensity of the spot is processed to transform into the image, which results in a quick count for the single molecule and a high accuracy of the count.

A further method for counting a single molecule is provided according to embodiments of the present disclosure. The method includes: inputting time sequence of an intensity of an spot; forming a line chart of time and intensity of the spot according to the time sequence, in which the line chart consists of a plurality of line segments; dividing the line chart into a plurality of grids in an array, counting the number of the line segments and/or ends of the line segments in each grid; subjecting the divided line chart to a line erosion according to numbers corresponding to the grids to transform the divided line chart to a simplified image; subjecting the simplified image to run-length coding to indicate connected domains; calculating an area of each connected domain, and determining that 1 is added to the number of the single molecules if the area of the connected domain is greater than a first predetermined threshold. According to the method for counting the single molecule, the line chart of the time sequence of the intensity of the spot is processed to transform into the image, which results in a quick count for the single molecule and a high accuracy of the count.

A device for identifying a single molecule is provided according to embodiments of the present disclosure. The device includes: an inputting unit configured to input time sequence of an intensity of an spot; a transforming unit configured to form a line chart of time and intensity of the spot according to the time sequence of the inputting unit, in which the line chart consists of a plurality of line segments; a grid counting unit configured to divide the line chart of the transforming unit into a plurality of grids in an array, and count the number of the line segments and/or ends of the line segments in each grid; a simplifying unit configured to subject the divided line chart to a line erosion according to numbers corresponding to the grids to transform the divided line chart to a simplified image; an indicating unit configured to subject the simplified image to run-length coding to indicate connected domains; a determining unit configured to calculate an area of each connected domain and determine that the connected domain corresponds to a single molecule if the area of the connected domain is greater than a first predetermined threshold. According to the device for identifying the single molecule, the line chart of the time sequence of the intensity of the spot is processed to transform into the image, which results in a quick identification for the single molecule and a high accuracy of the identification.

A device for counting a single molecule is provided according to embodiments of the present disclosure. The device includes: an inputting unit configured to input time sequence of an intensity of an spot; a transforming unit configured to form a line chart of time and intensity of the spot according to the time sequence of the inputting unit, in which the line chart consists of a plurality of line segments; a grid counting unit configured to divide the line chart of the transforming unit into a plurality of grids in an array, and count the number of the line segments and/or ends of the line segments in each grid; a simplifying unit configured to subject the divided line chart to a line erosion according to numbers corresponding to the grids to transform the divided line chart to a simplified image; an indicating unit configured to subject the simplified image to run-length coding to indicate connected domains; a determining unit configured to calculate an area of each connected domain and determine that the connected domain corresponds to a single molecule if the area of the connected domain is greater than a first predetermined threshold; a calculating unit configured to obtain a first number of the single molecules by calculation. According to the device for counting the single molecule, the line chart of the time sequence of the intensity of the spot is processed to transform into the image, which results in a quick count for the single molecule and a high accuracy of the count.

A device for counting a single molecule is provided according to embodiments of the present disclosure. The device includes: an inputting unit configured to input time sequence of an intensity of an spot; a transforming unit configured to form a line chart of time and intensity of the spot according to the time sequence of the inputting unit, in which the line chart consists of a plurality of line segments; a grid counting unit configured to divide the line chart of the transforming unit into a plurality of grids in an array, and count the number of the line segments and/or ends of the line segments in each grid; a simplifying unit configured to subject the divided line chart to a line erosion according to numbers corresponding to the grids to transform the divided line chart to a simplified image; an indicating unit configured to subject the simplified image to run-length coding to indicate connected domains; a determining unit configured to calculate an area of each connected domain and determine that 1 is added to the number of the single molecule if the area of the connected domain is greater than a first predetermined threshold. According to the device for counting the single molecule, the line chart of the time sequence of the intensity of the spot is processed to transform into the image, which results in a quick count for the single molecule and a high accuracy of the count.

A system for processing a single molecule is provided according to embodiments of the present disclosure. The system includes: a data inputting device configured to input data; a data outputting device configured to output data; a memory device configured to store data including a computer executable program; and a processor, configured to perform the computer executable program for performing a method for identifying a single molecule or a method for counting a single molecule described above. Thus, the identification and count of the single molecule may be achieved by the system for processing the single molecule.

A computer readable memory medium is also provided according to embodiments of the present disclosure. The computer readable memory medium is configured to store a program that, when executed by a computer, causes the computer to perform any method described above. The computer readable memory medium may be a read-only memory, a random access memory, a magnetic disc, an optical disc, etc.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference to the accompanying drawings, in which:

FIG. 14 is a schematic diagram of a line chart before a filtering in a method for identifying a single molecule according to an embodiment of the present disclosure;

FIG. 15 is a schematic diagram of a line chart after a filtering in a method for identifying a single molecule according to an embodiment of the present disclosure;

FIG. 16 is a line chart of a method for identifying a single molecule according to an embodiment of the present disclosure;

FIG. 19 is a schematic diagram showing line erosion in a method for identifying a single molecule according to an embodiment of the present disclosure;

FIG. 20 is a schematic diagram showing line erosion in a method for identifying a single molecule according to an embodiment of the present disclosure;

FIG. 21 is a schematic diagram of an eight connected domain in a method for identifying a single molecule according to an embodiment of the present disclosure;

FIG. 22 is a schematic diagram indicating a connected domain in a method for identifying a single molecule according to an embodiment of the present disclosure;

DETAILED DESCRIPTION

Figure 1:
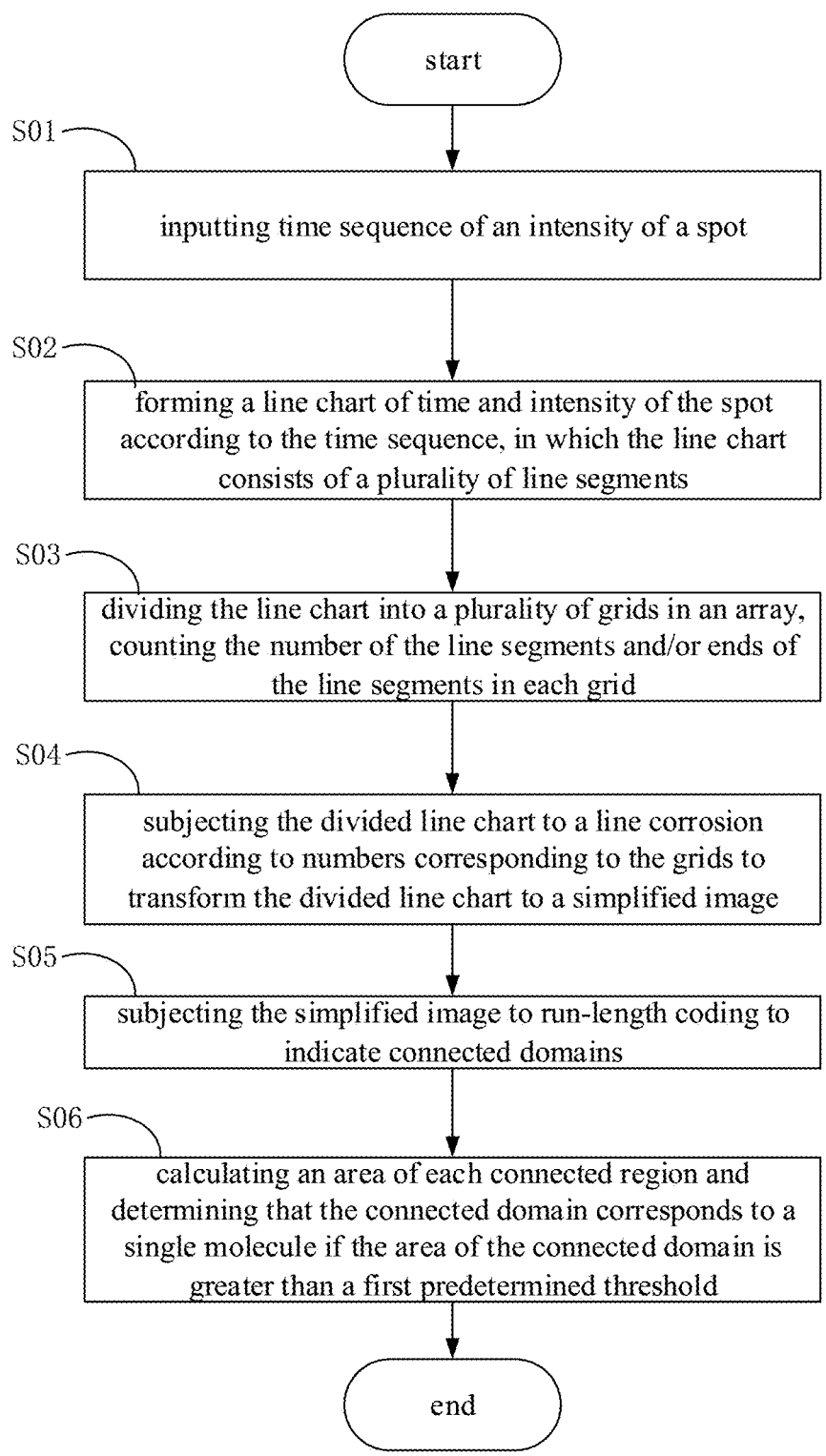
FIG. 1 is a flow chart of a method for identifying a single molecule according to an embodiment of the present disclosure.

Reference will be made in detail to embodiments of the present disclosure, where the same or similar elements and the elements having same or similar functions are denoted by like reference numerals throughout the descriptions. The embodiments described herein with reference to drawings are explanatory, illustrative, and used to generally understand the present disclosure. The embodiments shall not be construed to limit the present disclosure. Instead, the embodiments of the present disclosure include all the variants, modifications and their equivalents within the spirit and scope of the present disclosure as defined by the claims.

In the description of the disclosure, it should be understood that terms such as "first" and "second" are used herein for purposes of description and are not intended to indicate or imply relative importance or significance. Thus, the feature defined with "first" and "second" may include one or more this feature. In the description of the present disclosure, "a plurality of" means two or more than two, unless specified otherwise.

In the present disclosure, unless specified or limited otherwise, the terms "mounted," "connected," "coupled," "fixed" and the like are used broadly, and may be, for example, fixed connections, detachable connections, or integral connections; may also be mechanical or electrical connections; may also be direct connections or indirect connections via intervening structures; may also be inner communications of two elements, which can be understood by those skilled in the art according to specific situations.

Exemplary embodiments and examples are provided as follows to show different variations of the present disclosure. In order to keep the present disclosure brief, only certain embodiments, components and settings are described. For a purpose of simplicity and clear, reference numbers and/or reference letters may be repeatedly used in different examples of the present disclosure, while the reference numbers and the reference letters are not used to instruct the relationship between the various embodiments and/or configurations.

A method for identifying a single molecule and a method for counting a single molecule according to embodiments of the present disclosure may be used in gene sequencing. The term "gene sequencing" in embodiments of the present disclosure is the same as nucleic acid sequencing, including DNA sequencing and/or RNA sequencing, and including long fragment sequencing and/or short fragment sequencing.

As shown in FIG. 1, the method for identifying a single molecule according to an embodiment of the present disclosure includes: S01, inputting time sequence of an intensity of a spot; S02, forming a line chart of time and intensity of the spot according to the time sequence, in which the line chart consists of a plurality of line segments; S03, dividing the line chart into a plurality of grids in an array, counting the number of the line segments and/or ends of the line segments in each grid; S04, subjecting the divided line chart to a line erosion according to numbers corresponding to the grids to transform the divided line chart to a simplified image; S05, subjecting the simplified image to run-length coding to indicate connected domains; S06, calculating an area of each connected domain and determining that the connected domain corresponds to a single molecule if the area of the connected domain is greater than a first predetermined threshold. According to above method for identifying the single molecule, the line chart of the time sequence of the intensity of the spot is transformed into an image and further processed to run-length coding to obtain connected domains, thus resulting in a quick identification for the single molecules and a high accuracy of the identification. The method for identifying the single molecules based on the run-length coding may identify the single molecules accurately according to the time sequence data of the intensity of the spot, which is particularly suitable to the spot which contains less than 3 single molecules.

Specifically, in the step S01, when the spot is formed, the test sample is irradiated with a laser beam of a specific wavelength, and the test sample is excited to emit fluorescence, and then the fluorescence is collected by a camera to form an image containing the spot corresponding to the fluorescence emitted by the test sample, i.e., corresponding to a nucleic acid molecule. The term "spot" refers to a luminous point on the image, in which one luminous point occupies at least one pixel point, and the term "pixel point" refers to a pixel.

In an embodiment of the present disclosure, the image may be acquired from a single molecule sequencing platform from companies such as Helicos, Pacific Biosciences (PacBio). The original data after input is a parameter of the pixel point of the image, and the detection for the "spot" is detection for an optical signal of a single molecule.

Figure 2:
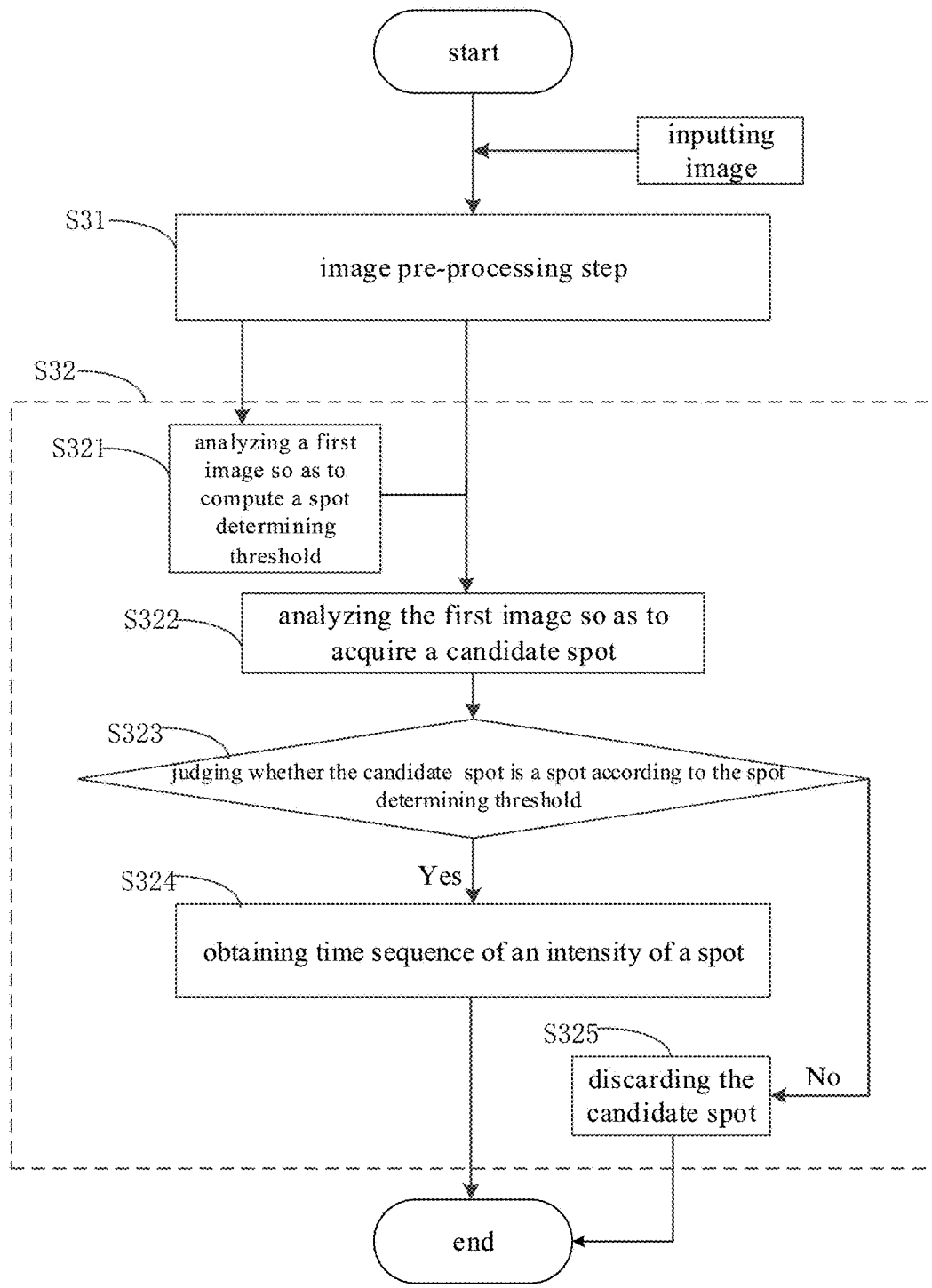
FIG. 2 is a flow chart of a method for identifying a single molecule according to an embodiment of the present disclosure.

As shown in FIG. 2, the method for identifying a single molecule according to an embodiment of the present disclosure also includes: an image pre-processing step S31, including: analyzing a to-be-processed image so as to obtain a first image, in which the to-be-processed image includes at least one spot having at least one pixel point; and a spot detecting step S32, including: step S321, analyzing the first image so as to compute a spot determining threshold; step S322, analyzing the first image so as to acquire a candidate spot; step S323, judging whether the candidate spot is the spot according to the spot determining threshold; S324, acquiring the time sequence of the intensity of the spot if the candidate spot is the spot, and step S325 discarding the candidate spot if the candidate spot is not the spot.

With the method for processing an image, the to-be-processed image is processed in the image pre-processing step, such that computation in the spot detecting step may be decreased. In addition, by judging whether the candidate spot is the spot according to the spot determining threshold, the accuracy of determining the spot is improved.

Specifically, in an example, an inputted to-be-processed image may be a 16-bit TIFF image of size 512*512 or 2048*2048, and the TIFF image may be a grayscale image. Thus, the processing procedure of this method may be simplified.

Figure 3:
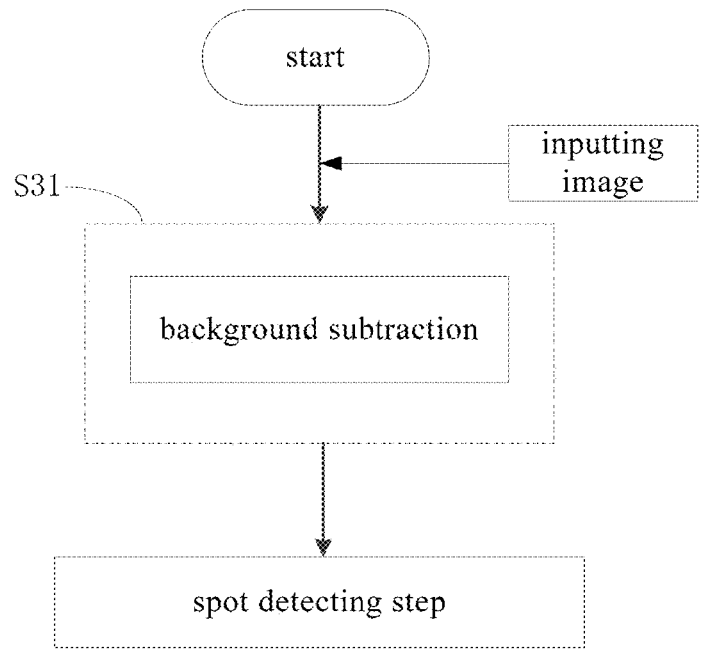
FIG. 3 is a flow chart of a method for identifying a single molecule according to an embodiment of the present disclosure.

Referring to FIG. 3, in some implementations of the present disclosure, the image pre-processing step S31 includes: performing a background subtraction on the to-be-processed image so as to acquire the first image. Thus, the noise of the to-be-processed image may be decreased, such that the accuracy of the method for identifying a single molecule is improved.

Figure 4:
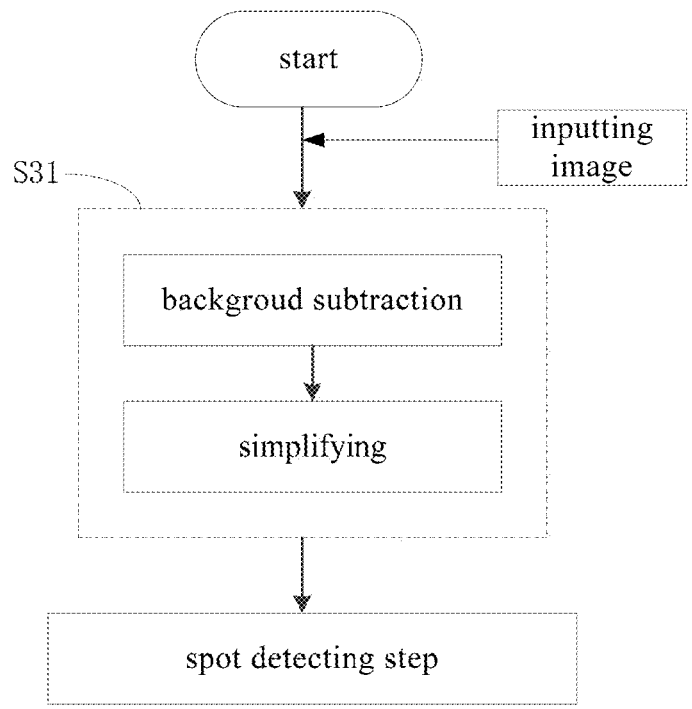
FIG. 4 is a flow chart of a method for identifying a single molecule according to an embodiment of the present disclosure.

Referring to FIG. 4, in some implementations of the present disclosure, the image pre-processing step S31 includes: simplifying the to-be-processed image after the background subtraction so as to acquire the first image. Thus, the computation in the subsequent steps of the method for identifying and/or counting single molecule may be decreased.

Figure 5:
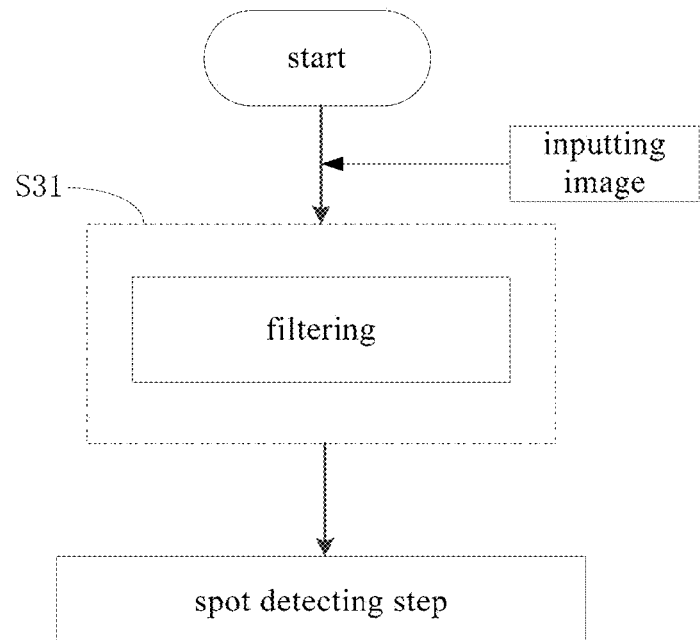
FIG. 5 is a flow chart of a method for identifying a single molecule according to an embodiment of the present disclosure.

Referring to FIG. 5, in some implementations of the present disclosure, the image pre-processing step S31 includes: filtering the to-be-processed image so as to acquire the first image. Thus, the first image may be acquired by filtering in case of maintaining image detail features to the greatest extent, such that the accuracy of the method for identifying and/or counting single molecules is improved.

Figure 6:
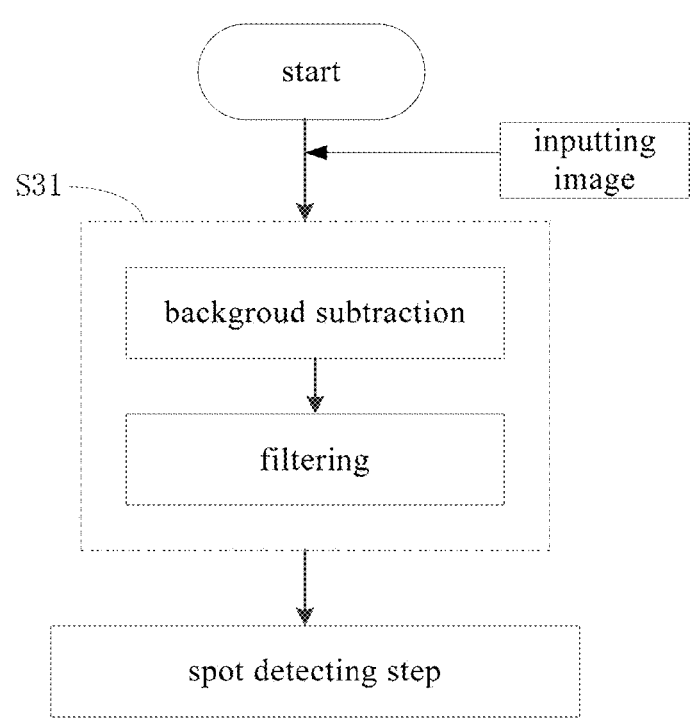
FIG. 6 is a flow chart of a method for processing an image in gene sequencing according to an embodiment of the present disclosure.

Referring to FIG. 6, in some implementations of the present disclosure, the image pre-processing step S31 includes: performing a background subtraction on the to-be-processed image, and then filtering, so as to acquire the first image. Thus, filtering the to-be-processed image after the background subtraction may further decrease the noise of the to-be-processed image, such that the accuracy of the method for identifying and/or counting single molecules is improved.

Figure 7:
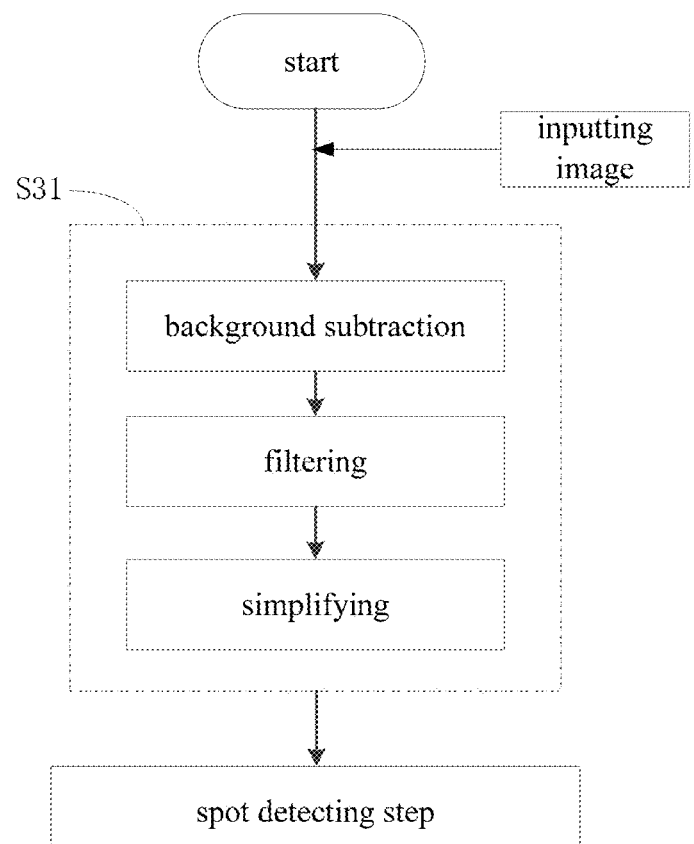
FIG. 7 is a flow chart of a method for identifying a single molecule according to an embodiment of the present disclosure.

Referring to FIG. 7, in some implementations of the present disclosure, the image pre-processing step S31 includes: simplifying the to-be-processed image after the background subtraction and the filtering so as to acquire the first image. Thus, the computation in the subsequent steps of the method for identifying and/or counting single molecules may be decreased.

Figure 8:
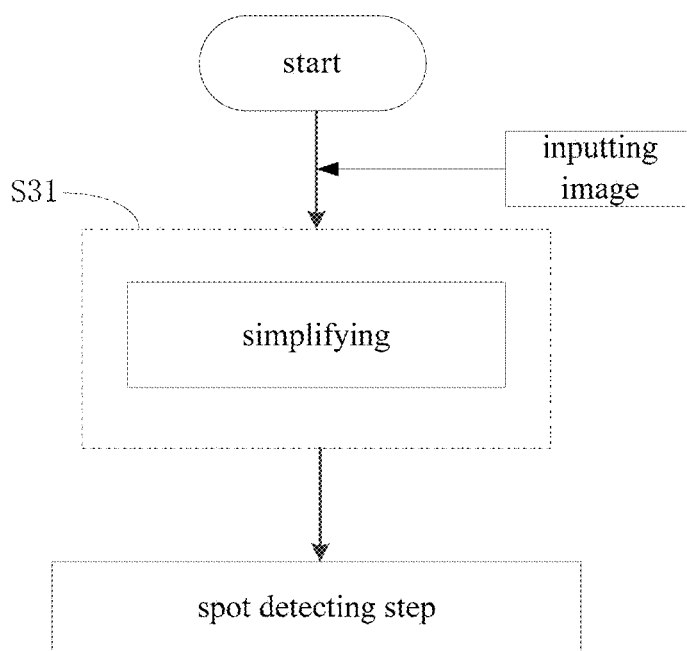
FIG. 8 is a flow chart of a method for identifying a single molecule according to an embodiment of the present disclosure.

Referring to FIG. 8, in some implementations of the present disclosure, the image pre-processing step S31 includes: simplifying the to-be-processed image so as to acquire the first image. Thus, the computation in the subsequent steps of the image processing method may be decreased.

In some implementations of the present disclosure, performing a background subtraction on the to-be-processed image includes: determining a background of the to-be-processed image by an opening operation; and performing the background subtraction on the to-be-processed image according to the background. In this way, the opening operation is for eliminating small objects, splitting objects at tenuous points and smoothing boundaries of big objects without changing the area of the image, such that the background subtracted image may be acquired precisely.

Specifically, in implementations of the present disclosure, the to-be-processed image (such as a grayscale image) is shifted by an a*a window (such as a 15*15 window), and the background of the to-be-processed image may be estimated using the opening operation (eroding first and expanding thereafter), as shown in formula 1 and formula 2:

$$g(x,y) = \text{erode}[f(x,y),B] = \min\{f(x+x',y+y') - B(x',y') | (x',y') \in D_b\}$$

formula 1 where g(x,y) represents a eroded grayscale image, f(x,y) represents the original grayscale image, and B represents a structural element;

$$g(x,y)=\text{dilate}[f(x,y),B]=\max\{f(x-x',y-y')-B(x',y')|(x',y') \in D_b\}$$ formula 2 where g(x,y) represents an expanded grayscale image, f(x,y) represents the original grayscale image, and B represents the structural element.

Therefore, the background noise may be acquired according to:

$$g=\text{imopen}(f(x,y),B)=\text{dilate}[\text{erode}(f(x,y),B)]$$ formula 3

The background subtraction is performed on the original image according to formula 4.

$$f=f-g=\{f(x,y)-g(x,y)|(x,y)\in D\}$$ formula 4

It should be noted that the specific methods of performing a background subtraction on the to-be-processed image in the present implementations may be applied to the steps of performing background subtraction on the image mentioned in any of the above-described implementations.

In some implementations of the present disclosure, performing the filtering is performing a Mexican Hat filtering. It is easy to perform the Mexican Hat filtering on an image and the cost of the method for identifying and/or counting single molecules may be reduced. Additionally, a contrast ratio of the foreground and the background may be improved by performing the Mexican Hat filtering, i.e., making the foreground brighter and the background darker.

The Mexican Hat filtering may be performed as follows: performing a Gaussian filtering on the to-be-processed image before the filtering using an m*m window, and performing a two-dimensional Laplacian sharpening on the to-be-processed image after the Gaussian filtering. m is a natural number and particularly, an odd number greater than 1. In this way, the Mexican Hat filtering may be accomplished by two steps.

Figure 9:
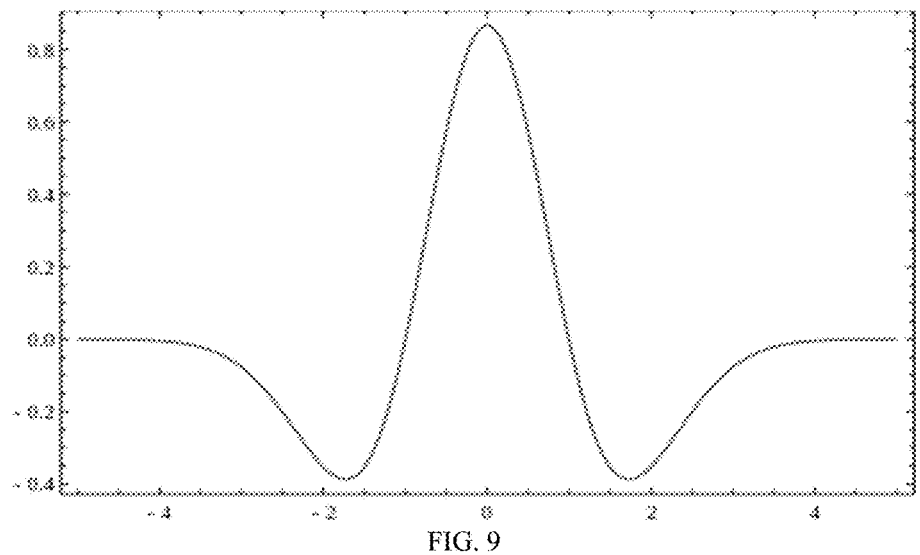
FIG. 9 is a schematic diagram of a curve of Mexican Hat kernel in the method for identifying a single molecule according to an embodiment of the present disclosure.

Specifically, referring to FIG. 9, the Mexican Hat kernel may be represented as the following formula.

$$\Psi(x,y) = \frac{1}{\pi\sigma^4}\left(1 - \frac{x^2+y^2}{2\sigma^2}\right)e^{-(x^2+y^2)/2\sigma^2}$$ formula 5 where x and y represent coordinates of the pixel point.

Firstly, the Gaussian filtering is performed on the to-be-processed image using the m*m window, as shown in formula 6.

$$f = \text{gaussBlur}(f_{m*m}) = \sum_{t1,t2 \in m/2} f(x+t1, y+t2) * w_{t1,t2}$$ formula 6 where t1 and t2 represent positions of the filter window, and $w_{t1,t2}$ represents a weight of Gaussian filtering.

Secondly, the two-dimensional Laplacian sharpening is performed on the to-be-processed image, as shown in formula 7.

$$\partial^2 f=[Kf(x,y)-kf(x-1,y-1)-kf(x-1,y+1)-kf(x+1,y-1)-kf(x+1,y+1)]$$ formula 7 where K and k are Laplacian operators with regard to a sharpen effect. K and k are modified if the sharpening needs to be strengthened or weakened.

In an example, m=3 and thus m*m=3*3, the formula 6 may written as $$f = \text{gaussBlur}(f_{3\times 3}) = \sum_{t1,t2 \in 3/2} f(x+t1, y+t2) * w_{t1,t2}$$

when performing the Gaussian filtering.

It should be noted that the specific methods of performing a Mexican Hat filtering on the to-be-processed image in the present implementations may be applied to the steps of performing Mexican Hat filtering on the image mentioned in any of the above-described implementations.

In some implementations of the present disclosure, the simplified image is a binary image. The binary image is easy to process and may be applied widely.

Specifically, in an example, a binary image may include 0 and 1 for indicating different pixel points with different attributes respectively, the binary image may be represented as $$BI = \begin{cases} 0 & \text{if condition 1 is satisfied} \\ 1 & \text{if condition 2 is satisfied} \end{cases}.$$

In some implementations of the present disclosure, the simplifying step includes: acquiring a signal-to-noise ratio (SNR) matrix according to the to-be-processed image before the simplifying, and simplifying the to-be-processed image before the simplifying according to the SNR matrix to obtain the first image.

In an example, a background subtraction is performed on the to-be-processed image to obtain a background subtracted image, and then a signal-to-noise ratio (SNR) matrix is acquired according to the background subtracted image. In this way, the image with less noise may be acquired and the accuracy of the method for processing an image may be improved. Specifically, in an example, the SNR matrix may be represented as $$SNR = R/MSE = r(x,y) / \left(\frac{1}{wh}\sum_i \sum_j (f(x_i,y_j) - \overline{f(x,y)})^2\right)$$

formula 8, where x and y represent coordinates of the pixel point, h represents a height of the image and w represents a width of the image, i∈w, j∈h.

Specifically, in an example, the simplified image is a binary image. The binary image may be acquired according to the SNR matrix, in which the binary image is represented as formula 9.

$$BI = \begin{cases} 0 & SNR > \text{mean}(SNR) \\ 1 & SNR <= \text{mean}(SNR) \end{cases}$$ formula 9

When computing the SNR matrix, the background subtraction and/or the filtering may be performed on the to-be-processed image, for example, the subtractive background processing step and/or the filtering processing step as described above. The background subtracted image is obtained according formula 4, and then a matrix of a ratio between the background subtracted image and the background may be acquired according to:

$$R = f/g = \{f(x,y)/g(x,y) | (x,y) \in D\} \quad \text{formula 10}$$

where D represents a dimension (height*width) of the image f.

Therefore, the SNR matrix may be acquired according to:

$$SNR = R/MSE = r(x,y) / \left( \frac{1}{wh} \sum_i \sum_j (f(x_i, y_j) - \overline{f(x,y)})^2 \right) \quad \text{formula 8}$$

In some implementation of the present disclosure, analyzing the first image so as to compute a spot determining threshold includes: processing the first image by an Otsu method so as to compute the spot determining threshold. In this way, the spot determining threshold may be found by a sophisticated and simple method, such that the accuracy of the method may be improved and the cost of the method may be reduced. In addition, by computing the spot determining threshold based on the first image, the efficiency and accuracy of the method may be improved.

Specifically, the Otsu method is also called as a maximum class square error method in which the image is split according to the maximum class square error, which means that a probability of wrong split is the minimum and the accuracy is high. It is assumed that a splitting threshold between the foreground and the background of the to-be-processed image is T, a number of the pixel points belonging to the foreground accounts for $\omega_0$ of the whole image, and the average gray level of the pixel points belonging to the foreground is $\mu_0$; a number of the pixel points belonging to the background accounts for $\omega_1$ of the whole image, and the average gray level of the pixel points belonging to the background is $\mu_1$. The average gray level of the to-be-processed image is $\mu$, and the class square error is var. Therefore, following formulas may be acquired.

$$\mu = \omega_0 * \mu_0 + \omega_1 * \mu_1 \quad \text{formula 11}$$

$$var = \omega_0(\mu_0 - \mu)^2 + \omega_1(\mu_1 - \mu)^2 \quad \text{formula 12}$$

Formula 13 is acquired by substituting the formula 11 into the formula 12.

$$var = \omega_0 \omega_1 (\mu_1 - \mu_0)^2 \quad \text{formula 13}$$

The splitting threshold T achieving the maximum class square error may be acquired by traversing, which may be configured as the spot determining threshold T.

Figure 10:
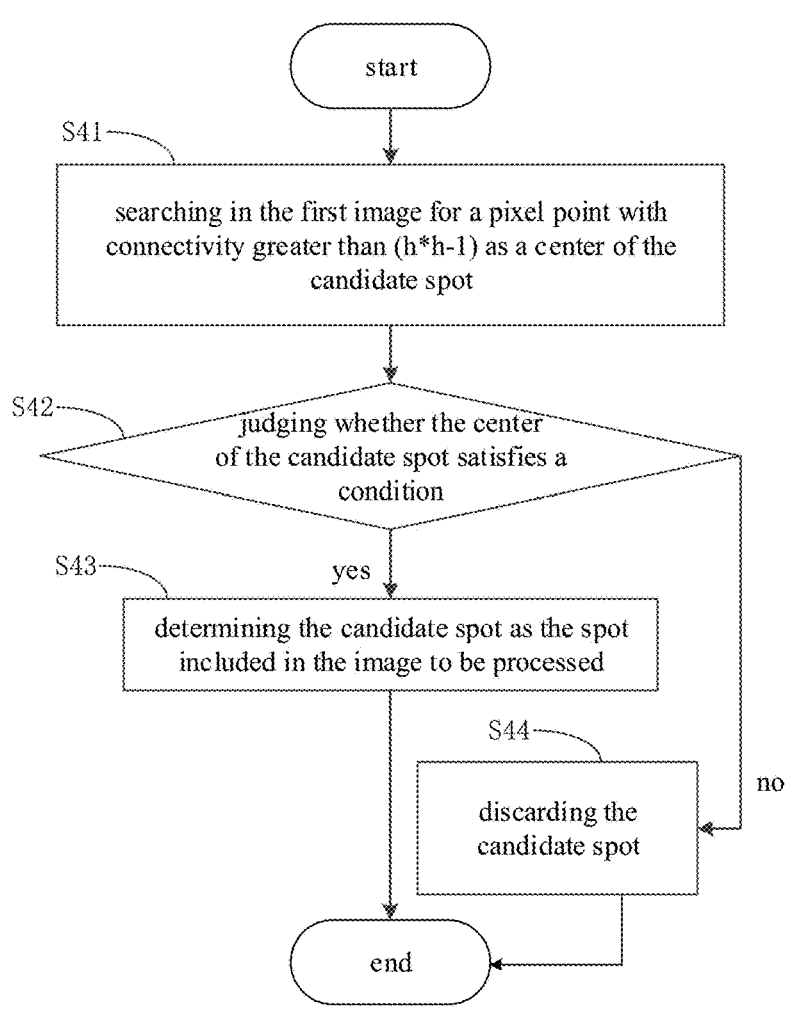
FIG. 10 is a flow chart of a method for identifying a single molecule according to an embodiment of the present disclosure.

In some implementations of the present disclosure, referring to FIG. 10, judging whether the candidate spot is the spot according to the spot determining threshold includes: step S41, searching in the first image for a pixel point with connectivity greater than (h*h−1) as a center of the candidate spot, in which there is a one-to-one correspondence between the h*h window and the spots, and each value in the h*h window corresponds to one pixel point; and step S42, judging whether the center of the candidate spot satisfies a condition of $I_{max} * A_{BI} * ceof_{guass} > T$, where $I_{max}$ is a maximum intensity of a center of the h*h window, $A_{BI}$ is a proportion of pixels in the first image being a set value in the h*h window, $ceof_{guass}$ is a correlation coefficient between a pixel in the h*h window and a two-dimensional Gaussian distribution, and T is the spot determining threshold, in which h is a natural number and particularly, an odd number greater than 1. The spot corresponding to the center of the candidate spot is determined as the spot included in the to-be-processed image if the condition is satisfied (step S43), and the spot corresponding to the center of the candidate spot is discarded if the condition fails to be satisfied (step S44). In this way, the detection of the spot may be achieved.

Figures 11, 12, 13:
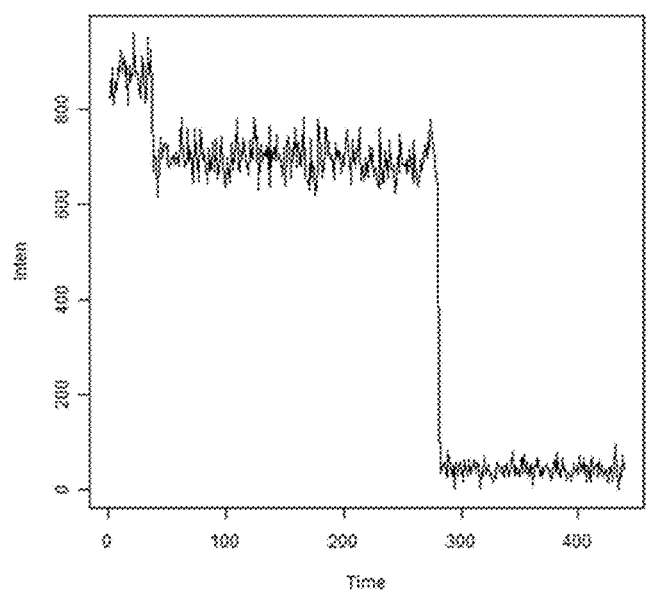
FIG. 11 is a schematic diagram of eight connection pixels in a method for identifying a single molecule according to an embodiment of the present disclosure.
FIG. 12 is a line chart of a method for identifying a single molecule according to an embodiment of the present disclosure.
FIG. 13 is a schematic diagram showing that a line chart is divided into a plurality of grids in a method for identifying a single molecule according to an embodiment of the present disclosure.

Specifically, $I_{max}$ may be understood as the maximum intensity of the center of the candidate spot. In an example, h=3. Referring to FIG. 11, the pixel point with 8 connected domain is searched as the pixel point of the candidate spot. $I_{max}$ may be the maximum intensity of the center of 3*3 window, $A_{BI}$ is a proportion of pixels in the first image being a set value in the 3*3 window, and $ceof_{guass}$ is a correlation coefficient between a pixel in the 3*3 window and the two-dimensional Gaussion distribution.

The first image can be the image after the simplifying, such as the binary image. The set value in the binary image may be the value corresponding to the pixel specifying a set condition. In another example, the binary image may include 0 and 1 for indicating different pixel points with different attributes respectively. If the set value is 1, $A_{BI}$ is a proportion of pixels in the binary image being 1 in the h*h window. For example, BI=1 when SNR<=mean (SNR).

In some implementations of the present disclosure, the value of p can be set as the value of m which is used in the Mexican Hat filtering, i.e. h=m. In some embodiments of the present disclosure, during the collection for forming above described image, the camera collects the fluorescence in a plurality of fields of view (FOV) in sequence according to the time sequence. Therefore, when the image data is obtained, the intensity of the spot included in the image data corresponds to the time sequence collected by the camera.

In the step S02, after the spots are obtained, points of intensities of the spots of adjacent collection times are connected by a line, thus forming a line chart of time and intensity of the spot as shown in FIG. 12. In FIG. 12, the horizontal axis represents the time of collection of fluorescence, in milliseconds (ms), and the vertical axis represents the intensity of the spots. In an example, the time interval between two adjacent collections of fluorescence is 20 ms.

In an embodiment of the present disclosure, the vertical axis corresponds to values of the intensities of the spots, and the value of the intensity of the spot is a value of the pixel. For a 16-bit TIFF image, the value of the spot pixel is in the range of 0 to 65535. For an 8-bit grayscale image, the value of the spot pixel is in the range of 0 to 255. The 16-bit image is used in the present disclosure.

In the step S03, waveform of the line chart is processed, such that the run-length coding may be performed subsequently. During processing, the line chart is divided into a plurality of grids.

In some embodiments of the present disclosure, the line chart is divided according to a time frame of the intensity when collected and a magnitude of the intensity. In this case, the line chart may be divided into grids easily to reduce the cost of the method for identifying the single molecule. Specifically, the line chart is divided into M*N grids, in which M is determined by dividing according to the time frame and N is determined by dividing according to the magnitude of the intensity. The time frame of the collected intensity is the time interval of adjacent collections of the fluorescence. In an embodiment of the present disclosure, a direction along the horizontal axis refers to a length direction of a grid and a direction along the vertical axis refers to a height direction of a grid. The length of the grid may be set as times of the time frame, such as 1 times, 2 times and 2.5 times. The height of the grid may be set flexibly. For example, for the 16-bit TIFF image, the value of the vertical axis is in the range of 0 to 65535. When grids are divided, the values of the vertical axis are normalized and then divided into 50 parts, such that the height of the grid may be set as 0.02, i.e., N=50.

In an embodiment of the present disclosure, the time interval between two adjacent collections of fluorescence is 20 ms, and the length of one grid is equal to one time interval, i.e., the height=0.02. As shown in FIG. 16, the number of one line segment in one grid may be 0, 1 or 2. In FIG. 16, the point represents time sequence of the intensity of the spot.

In an embodiment of the present disclosure, as shown in FIG. 13, the line chart is divided into 8*6 grids and the number of the line segments and/or ends of the line segments in each grid is counted. In FIG. 13, the number of line segments in each grid is counted (i.e., the number of the times segments passing through each grid). Number in each grid represents the number of the segments in each grid. In FIG. 13, the point represents time sequence of the intensity of the spot.

In line erosion, a formula may be used to perform morphological operation of erosion: $g(x,y)=erode[f(x,y), B]=\min\{f(x+x',y+y')-B(x',y')|(x',y')\in D_b\}$. Optionally, a line-shape element may be used, such as a W*1 window. If the number of the grid of the window is greater than a threshold T, the gird is indicated as a first value, otherwise, the gird is indicated as a second value. In this case, the line chart may be divided as a simplified image containing grids with the first value or the second value. In some embodiments of the present disclosure, the simplified image is a binary image. For example, the first value may be 1, and the second value may be 0.

In an embodiment of the present disclosure, as shown in FIG. 19, a length of a gird is L1, W=2*L1 and T=2. FIG. 19 shows 5 grids arranged in the length direction, and the number in each grid represents the number of such a grid. In this case, when the line erosion is performed, the window is aligned to the grid, and after the line erosion, the 5 grids are indicated as 0, 1, 0, 0, and 0, respectively.

In an embodiment of the present disclosure, as shown in FIG. 19, a length of a grid is L1, W=2*L1 and T=2. FIG. 19 shows 5 grids arranged in the length direction, and the number in each grid represents the number of such a grid. In this case, when the line erosion is performed, the window and the grid are arranged in a staggered form, and after the line erosion, the 5 grids are indicated as 0, 1, 0, 0, and 0, respectively.

It should be noted that W is greater than or equal to the length of one grid. Optionally, W is an integer multiple of the length of one grid. In an embodiment of the present disclosure, W≥L1. Optionally, W is an integer multiple of L1.

In some embodiments of the present disclosure, the threshold T is in a range [6, 8] dependent on undulation of the waveform of the line chart. Specifically, the smaller the undulation is, the greater the threshold T is.

For ease of understanding, when run-length coding is described, the following description is made by taking 1 and 0 in the binary image as an example. It should be understood that modifications may be made by one skilled in the art, for example, to use another type of the simplified image and values except for the first and second values.

In run-time coding, an eight connection manner may be used. According to the eight connection principle, grids are connected to form the connected domain by a recursive algorithm and then the connected domain is indicated by using run-length coding. Specifically, according to an eight connection, for example, a 3*3 window used as shown in FIG. 21, a grid Q with a number which is not zero is selected to start with, if other eight grids in eight directions are not zero, the eight grids are indicated as the same number of the grid Q. By that analogy, a completed simplified image may be the indicated image as shown in FIG. 22.

In FIG. 22, different connected domains are indicated by different values. When the area of each connected domain is calculated, the number of times of occurrence of the same number is recorded as the area of the connected domain. As shown in FIG. 22, the number 9 appears 9 times, such that the area of the connected area corresponding to the number 9 is 9, and the number 7 appears 20 times, the area of the connected domain corresponding to the number 7 is 20.

In the above embodiment, a recursive algorithm is used. In other examples, a traversal algorithm may also be used to define the connected domain.

If the area of the connected domain is greater than a first determined threshold P, the connected domain corresponds to a single molecule. The value of P is related to the decay time of single molecule fluorescence. In one example, the first determined threshold P is in the range [5, 10].

Figure 18:
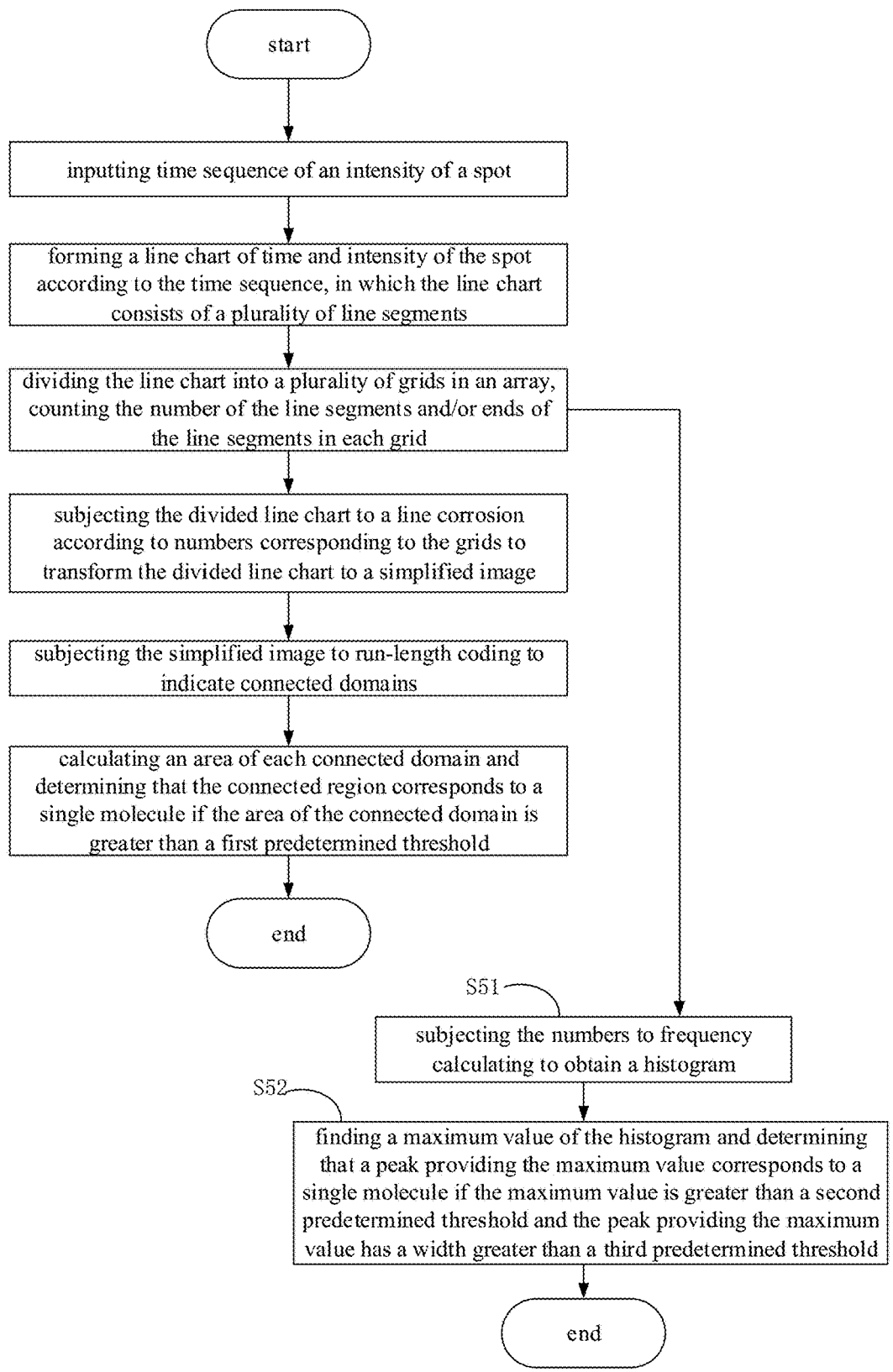
FIG. 18 is a flow chart of a method for identifying a single molecule according to an embodiment of the present disclosure.

In some embodiments of the present disclosure, with reference to FIG. 18, the method for identifying the single molecule may further include: S51, dividing the intensity in groups according to a magnitude of the intensity to subject the numbers to frequency calculating to obtain a histogram; S52, finding a maximum value of the histogram, and determining that a peak providing the maximum value corresponds to a single molecule if the maximum value is greater than a second predetermined threshold and the peak providing the maximum value has a width greater than a third predetermined threshold.

As described above, the method for identifying the single molecule may thus be applied more widely. The method for identifying the single molecule based on the histogram can identify single molecule accurately according to data of the intensity and time sequence of the spot, and particularly suitable to the spot containing more than 3 single molecules. In such an embodiment, the method based on the histogram and the method based on run-length coding may be combined to identify single molecules in the line chart (time sequence of the intensity of the spot) having different waveforms accurately.

In some embodiments of the present disclosure, S51 further includes: dividing the intensity in N groups according to the magnitude of the intensity and calculating frequencies of the number in the N groups:

$$n_i = \sum_{0<=j<=M} g_{i,j}, 0 <= i <= N,$$

in which $n_i$ represents a sum of the frequencies of the numbers of an $i^{st}$ line of the grids, j represents a time frame, $g_{ij}$ represents a frequency of the number of grid (i,j), and M represents the number of the time frames.

Specifically, in an embodiment, a horizontal axis of the histogram represents the number of a group, and a vertical axis of the histogram represents a frequency of the number in each group. It should be noted that the value of N is equal to the value of N in M*N grids formed above, and the value of M is equal to the value of M in M*N grids formed above.

In some embodiments, the step of dividing the intensity in groups according to the magnitude of the intensity to subject the numbers to frequency calculating to obtain the histogram includes: equalizing the histogram with a L-shaped window:

$$n'_i = \sum_{i-L/2 <= p <= i+L/2} n_p, 0 <= i <= N,$$

in which $n_p$ represents equalization of $n_i$, $n_i$ represents a sum of results of the equalization of $n_i$, and p represents an integer associated with the size of the L-shaped window and the $i^{st}$ line. Thus, the histogram is distributed more uniformly to be identified easily. L-shaped window is used for equalization of the histogram, and the value of L is related to the size of the L-shaped window and the $i^{st}$ line. In general, if the single molecule has a fast fluorescence quenching, the value of L should not be too large. The accuracy of the histogram is affected by the size of the L-shaped window, and the value of L can be set flexibly to select appropriate histogram accuracy. In one embodiment, the value of L is in a range [5, 15].

Figure 17:
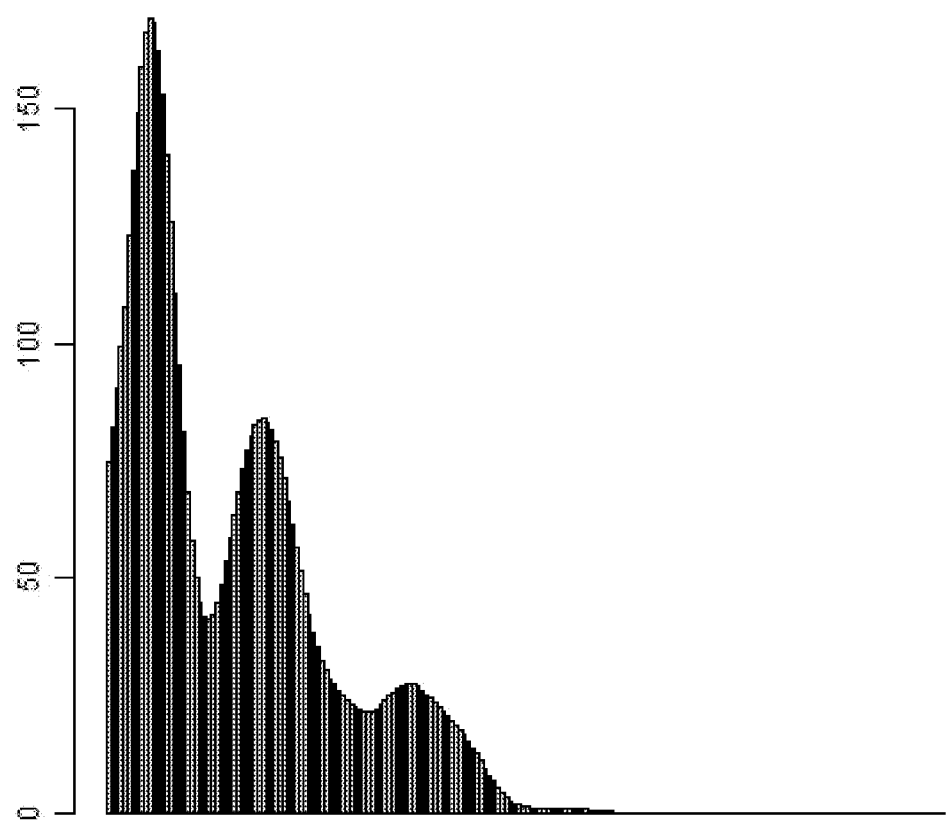
FIG. 17 is a histogram after equalization in a method for identifying a single molecule according to an embodiment of the present disclosure.

With reference to FIG. 17 being a histogram after equalization, a horizontal axis of the histogram represents the number of a group, and a vertical axis of the histogram represents a frequency of the number in each group.

In the step 52, all the maximum values of the histogram may be calculated by derivation. The second determined threshold Q and the third determined threshold H are related to the shape of the peak of the line chart. Specifically, the sharper the peak is, the greater the second determined threshold Q is, and the smaller the third determined threshold H is. The gentler the peak is, the smaller the second determined threshold Q is, the greater the third determined threshold H is. In an embodiment, the second determined threshold Q is in a range [2, 6], and the third determined threshold H is in the range [4, 10].

In an embodiment of the present disclosure, the maximum value is a top value of the peak (i.e., an inflexion point). In other words, if the maximum value in the peak meets certain conditions, the peak corresponds to a single molecule.

In some embodiments of the present disclosure, before the line chart is divided, the method for identifying the single molecule further includes: performing a filtering to the line chart, such that it is possible to eliminate the abrupt error caused by the intensity flicker and the camera sampling, and the waveform of the line graph is smoother. In particular, the modification of the waveform may be performed by using a median value of a window of a size of L2 for filtering: R=medium($Z_i$). In an embodiment, with reference to FIG. 14 being a line chart before filtering and FIG. 15 being a line chart after filtering, it can be seen from the figures that the waveform of the filtered line chart is more smooth, which facilitates to improve the accuracy and efficiency of single molecule identification.

Figure 23:
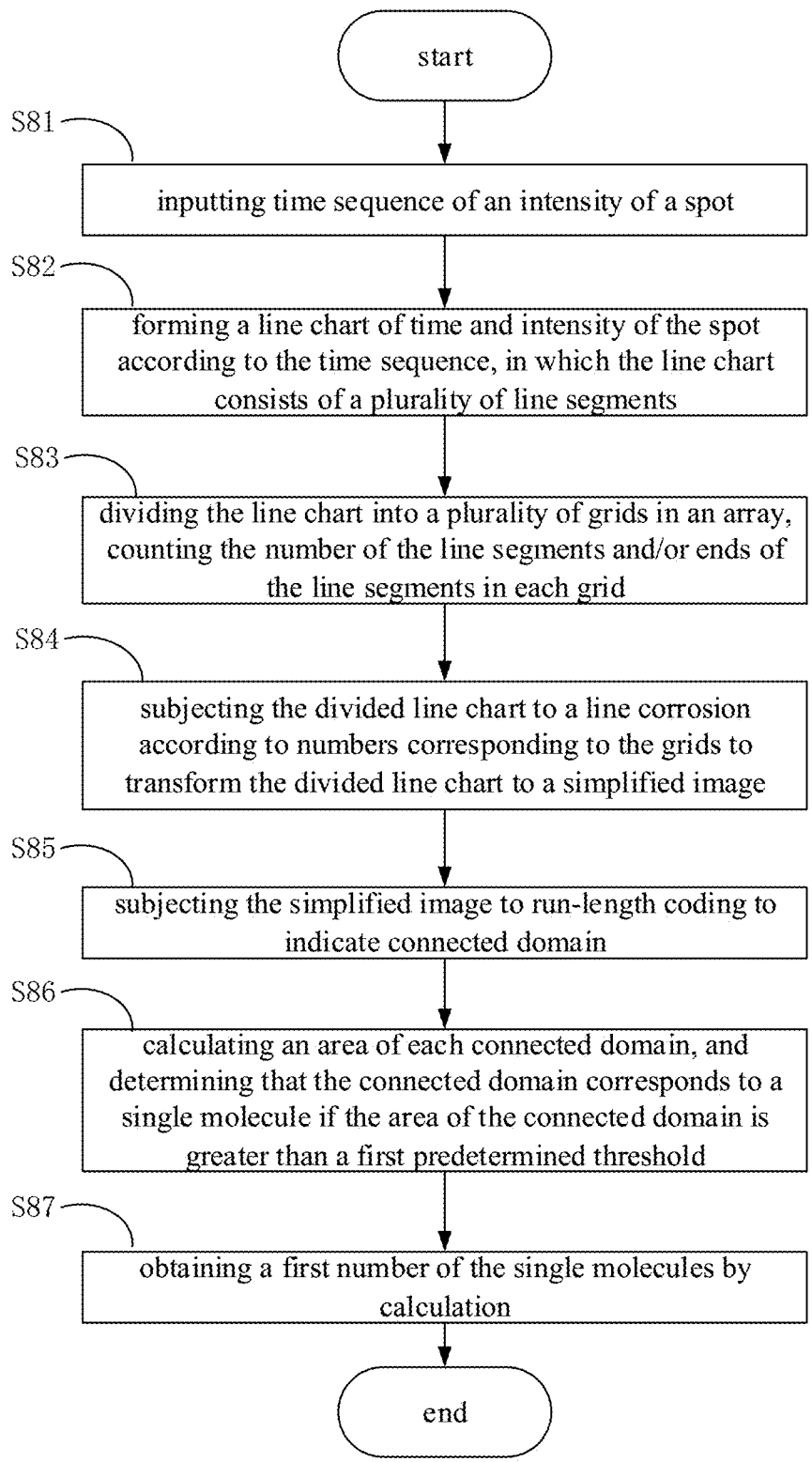
FIG. 23 is a flow chart of a method for counting a single molecule according to an embodiment of the present disclosure.

With reference to FIG. 23, a method for counting the single molecule according to an embodiment of the present disclosure includes: S81, inputting time sequence of an intensity of an spot; S82, forming a line chart of time and intensity of the spot according to the time sequence, in which the line chart consists of a plurality of line segments; S83, dividing the line chart into a plurality of grids in an array, counting the number of the line segments and/or ends of the line segments in each grid; S84, subjecting the divided line chart to a line erosion according to numbers corresponding to the grids to transform the divided line chart to a simplified image; S85, subjecting the simplified image to run-length coding to indicate connected domains; S86, calculating an area of each connected domain, and determining that the connected domain corresponds to a single molecule if the area of the connected domain is greater than a first predetermined threshold; S87, obtaining a first number of the single molecules by calculation. According to the method for counting the single molecule, the line chart of the time sequence of the intensity of the spot is processed to transform into the image, thus obtaining the connected domains by run-length coding, which results in a quick count for the single molecule and a high accuracy of the count. It should be noted that the description of the technical features and advantages of methods for identifying and/or counting the single molecule in any one of the above embodiments and examples, including explanations and descriptions of steps, parameter settings, and image pre-processing spot detection, is also applicable to the method for counting the single molecule in embodiments of the present embodiment. In order to avoid redundancy, it is not further described in detail here.

Figure 24:
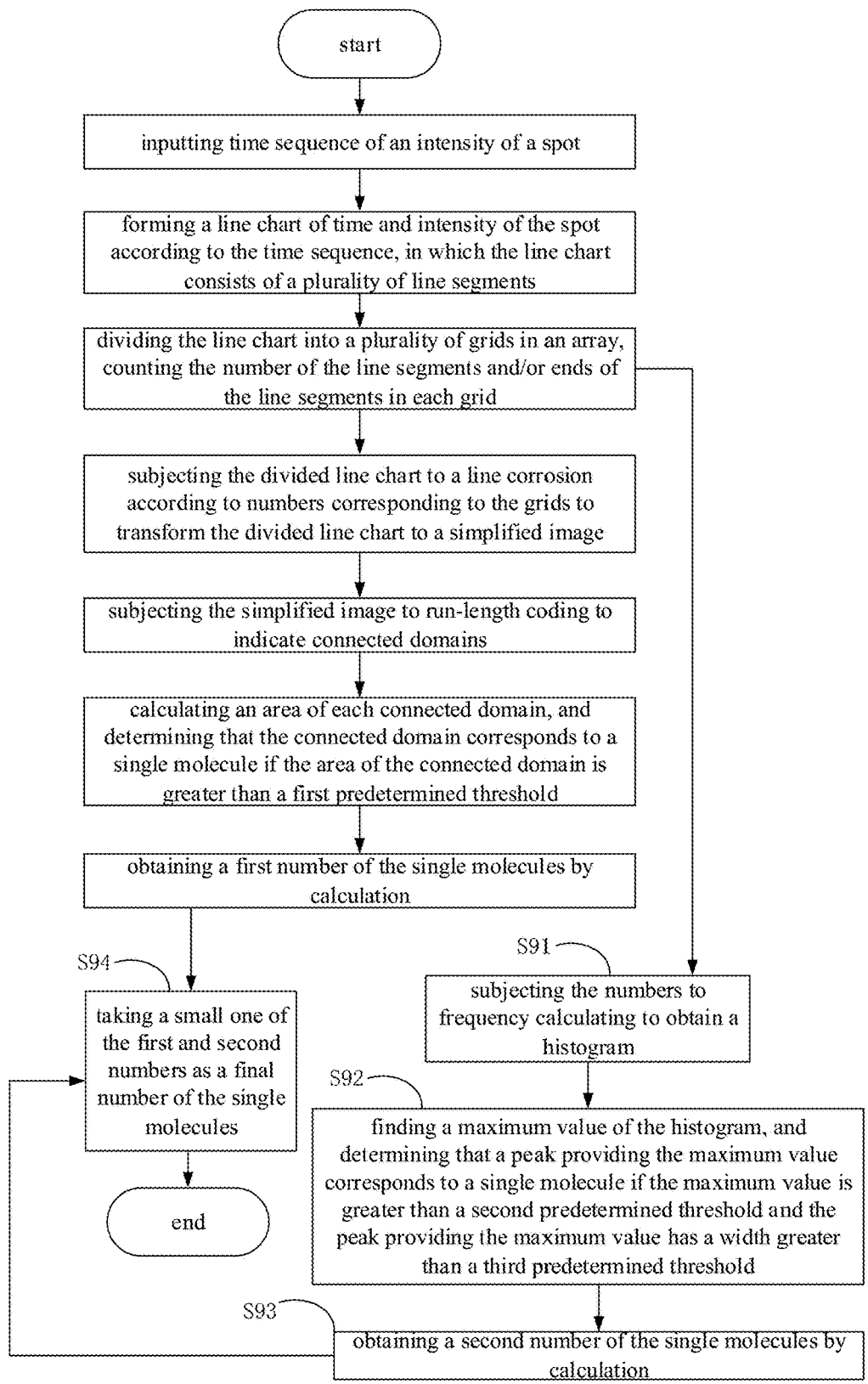
FIG. 24 is a flow chart of a method for counting a single molecule according to an embodiment of the present disclosure.

For example, in an embodiment of the present disclosure, before S83, the method for counting the single molecule may further include filtering the line chart. In another embodiment, as shown in FIG. 24, the method for counting the single molecule further includes: S91, dividing the intensity in groups according to a magnitude of the intensity to subject the numbers to frequency calculating to obtain a histogram; S92, finding a maximum value of the histogram, and determining that a peak providing the maximum value corresponds to a single molecule if the maximum value is greater than a second predetermined threshold and the peak providing the maximum value has a width greater than a third predetermined threshold; S93, obtaining a second number of the single molecules by calculation; and S94, taking a small one of the first and second numbers as a final number of the single molecules. The method for counting the single molecule based on the histogram calculation is particularly suitable to accurately find the spot containing more than 3 single molecules. The method for counting the single molecules based on the run-length coding is particularly suitable to accurately find the spot which contains ≤3 single molecules. In an embodiment, above two methods may be combined, and the single molecule of the line chart with different waveforms may be found and counted accurately. In an embodiment, the simplified image is a binary image.

Figure 25:
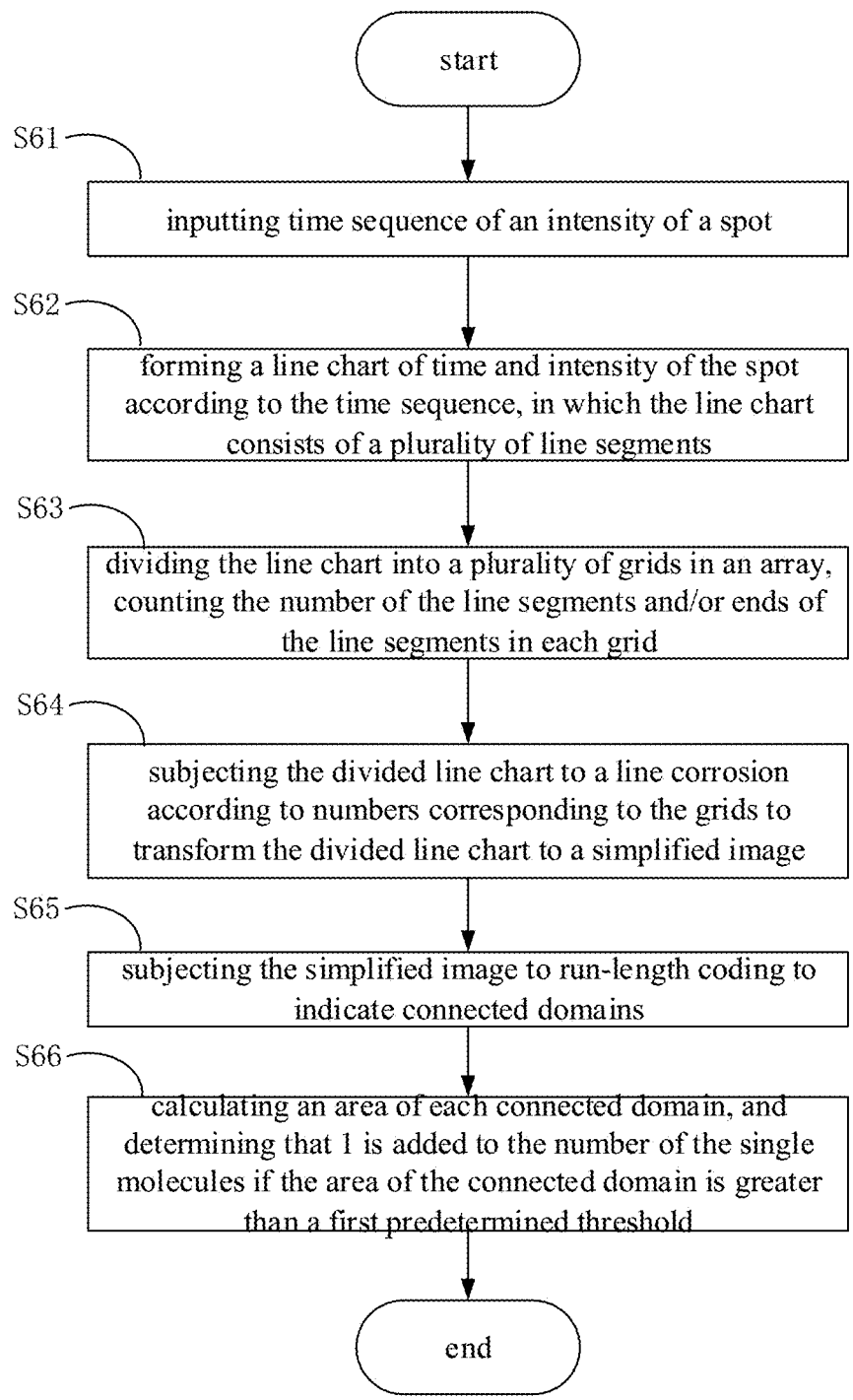
FIG. 25 is a flow chart of a method for counting a single molecule according to an embodiment of the present disclosure.

As shown in FIG. 25, a method for counting the single molecule according to an embodiment of the present disclosure includes: S61, inputting time sequence of an intensity of an spot; S62, forming a line chart of time and intensity of the spot according to the time sequence, in which the line chart consists of a plurality of line segments; S63, dividing the line chart into a plurality of grids in an array, counting the number of the line segments and/or ends of the line segments in each grid; S64, subjecting the divided line chart to a line erosion according to numbers corresponding to the grids to transform the divided line chart to a simplified image; S65, subjecting the simplified image to run-length coding to indicate connected domains; S66, calculating an area of each connected domain, and determining that 1 is added to the number of the single molecules if the area of the connected domain is greater than a first predetermined threshold.

According to the method for counting the single molecule, the line chart of the time sequence of the intensity of the spot is processed to transform into the image, thus obtaining the connected domains by run-length coding, which results in a quick count for the single molecule and a high accuracy of the count.

It should be noted that the description of the technical features and advantages of methods for identifying and/or counting the single molecule in any one of the above embodiments and examples, including explanations and descriptions of steps, parameter settings, and image pre-processing spot detection, is also applicable to the method for counting the single molecule in embodiments of the present embodiment. In order to avoid redundancy, it is not further described in detail here.

Figure 26:
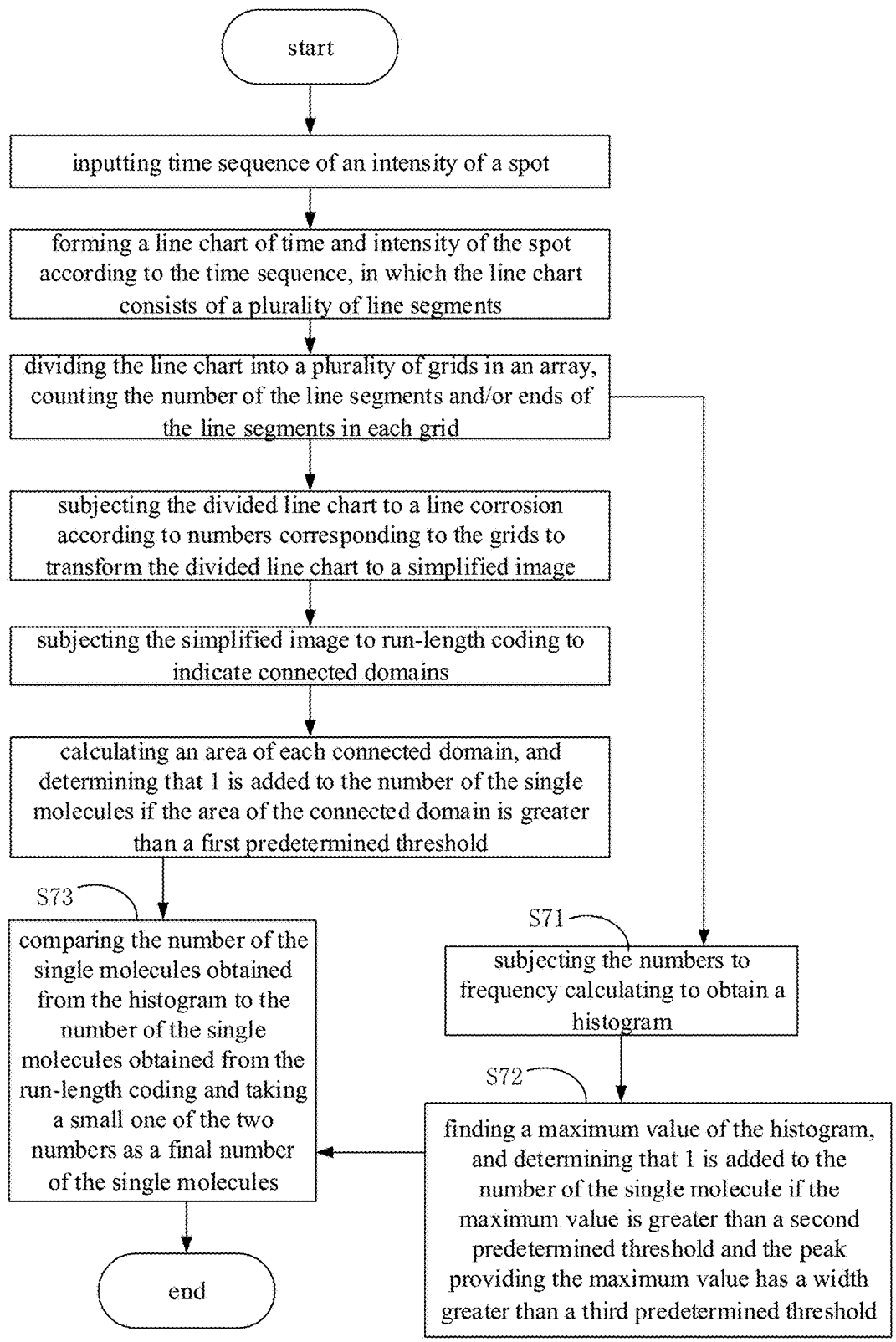
FIG. 26 is a flow chart of a method for counting a single molecule according to an embodiment of the present disclosure.

For example, in some embodiments, before S63, the method for counting the single molecule may further include filtering the line chart. In another embodiment, as shown in FIG. 26, the method for counting the single molecule further includes: S71, dividing the intensity in groups according to a magnitude of the intensity to subject the numbers to frequency calculating to obtain a histogram; S72, finding a maximum value of the histogram, and determining that 1 is added to the number of the single molecule if the maximum value is greater than a second predetermined threshold and the peak providing the maximum value has a width greater than a third predetermined threshold; S73, comparing the number of the single molecules obtained from the histogram to the number of the single molecules obtained from the run-length coding and taking a small one of the two numbers as a final number of the single molecules. Thus, the method for counting the single molecule may be applied widely and a more accurate number of the single molecules may be achieved.

The method for counting the single molecule based on the histogram calculation is particularly suitable to accurately find the spot containing more than 3 single molecules. The method for counting the single molecules based on the run-length coding is particularly suitable to accurately find the spot which contains ≤3 single molecules. In an embodiment, above two methods may be combined, and the single molecule of the line chart with different waveforms may be found and counted accurately. For example, the number of the single molecules based on the run-length coding is the first number and the number of the single molecules based on the histogram is the second number. The first number is compared to the second number and the smaller one of these two numbers is taken as the final number of the single molecules.

Figure 27:
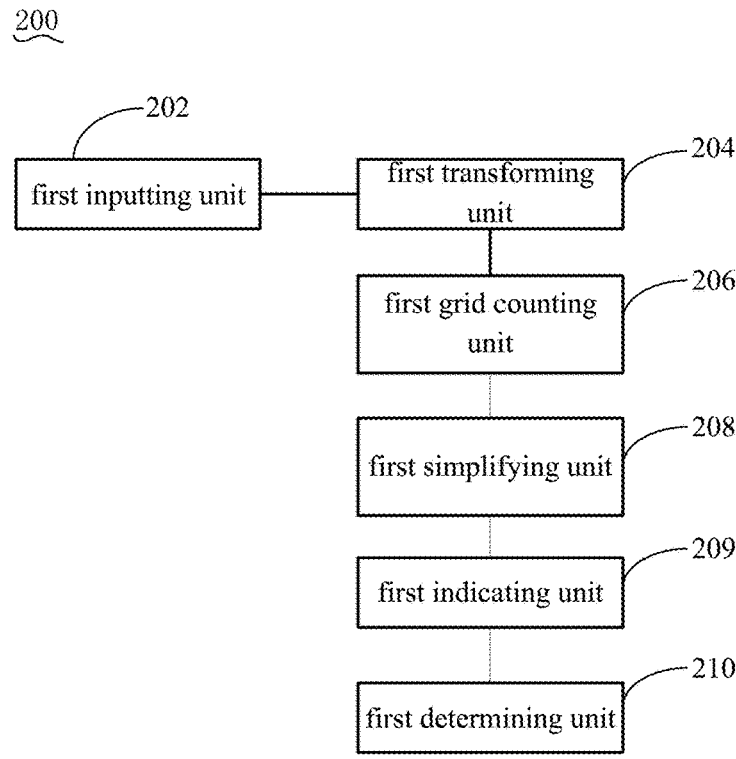
FIG. 27 is a block diagram of a device for identifying a single molecule according to an embodiment of the present disclosure.

As shown in FIG. 27, a device 200 for identifying a single molecule according to embodiments of the present disclosure is used to perform all of or part of the methods for identifying the single molecule according to any embodiment or example described above. The device 200 for identifying the single molecule includes: a first inputting unit 202 configured to input time sequence of an intensity of an spot; a first transforming unit 204 configured to form a line chart of time and intensity of the spot according to the time sequence of the first inputting unit 202, in which the line chart consists of a plurality of line segments; a first grid counting unit 206 configured to divide the line chart of the first transforming unit 204 into a plurality of grids in an array, and count the number of the line segments and/or ends of the line segments in each grid; a first simplifying unit 208 configured to subject the divided line chart to a line erosion according to numbers corresponding to the grids to transform the divided line chart to a simplified image; a first indicating unit 209 configured to subject the simplified image to run-length coding to indicate connected domains; a first determining unit 210 configured to calculate an area of each connected domain and determine that the connected domain corresponds to a single molecule if the area of the connected domain is greater than a first predetermined threshold. According to the device 200 for identifying the single molecule, the line chart of the time sequence of the intensity of the spot is processed to transform into the image, thus obtaining the connected domains by run-length coding, which results in a quick identification for the single molecule and a high accuracy of the identification.

In an embodiment, the simplified image is a binary image.

Figure 28:
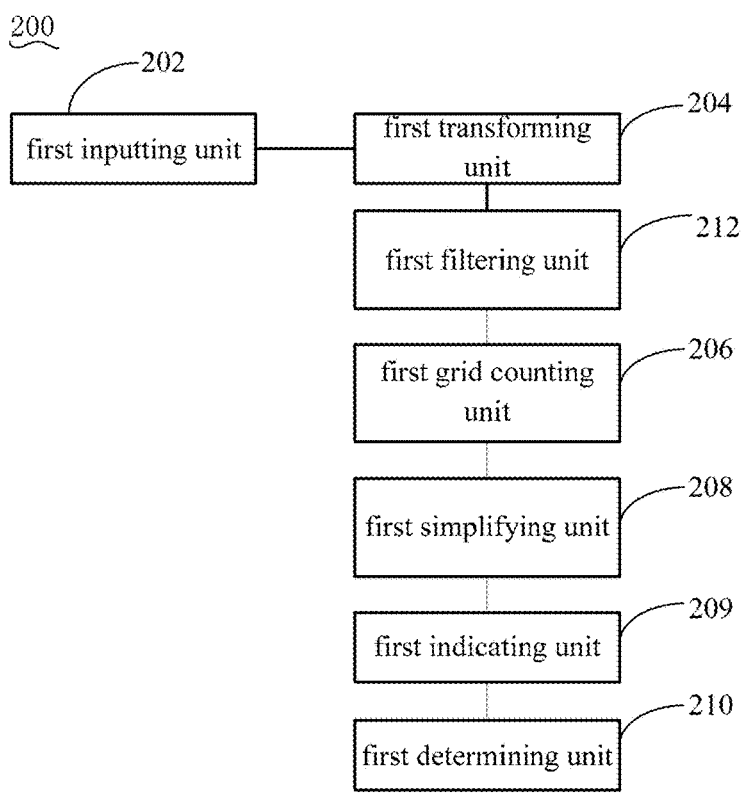
FIG. 28 is a block diagram of a device for identifying a single molecule according to an embodiment of the present disclosure.

It should be noted that the description of the technical features and advantages of the method for identifying the single molecule in any one of the above embodiments and examples is also applicable to the device 200 for identifying the single molecule in embodiments of the present embodiment. In order to avoid redundancy, it is not further described in detail here. For example, in some embodiments, as shown in FIG. 28, the device 200 for identifying the single molecule further includes a first filtering unit 212 connected to the first grid counting unit 206, configured to filter the line chart of the first transforming unit 204 before the line chart is divided in the plurality of grids in the array.

In some embodiments of the present disclosure, in the first grid counting unit 206, the line chart is divided according to a time frame of the intensity when collected and a magnitude of the intensity.

Figure 29:
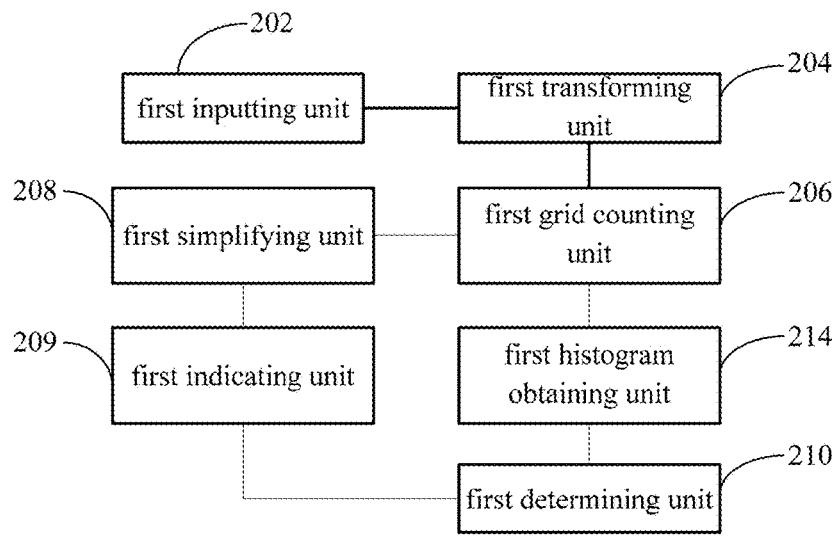
FIG. 29 is a block diagram of a device for identifying a single molecule according to an embodiment of the present disclosure.

Referring to FIG. 29, in some embodiments of the present disclosure, the device 200 for identifying a single molecule also includes: a first histogram obtaining unit 214 configured to divide the intensity in groups according to a magnitude of the intensity to subject the numbers to frequency calculating to obtain a histogram; in the first determining unit 210, finding a maximum value of the histogram, and determining that a peak providing the maximum value corresponds to a single molecule if the maximum value is greater than a second predetermined threshold and the peak providing the maximum value has a width greater than a third predetermined threshold.

In some embodiments of the present disclosure, in first histogram obtaining unit 214, dividing the intensity in groups according to a magnitude of the intensity to subject the numbers to frequency calculating to obtain a histogram includes: dividing the intensity in N groups according to the magnitude of the intensity and calculating frequencies of the number in the N groups:

$$n_i = \sum_{0<=j<=M} g_{i,j}, 0 <= i <= N,$$

in which $n_i$ represents a sum of the frequencies of the numbers of an $i^{st}$ line of the grids, j represents a time frame, $g_{ij}$ represents a frequency of the number of grid (i,j), and M represents the number of the time frames.

In some embodiments, in first histogram obtaining unit 214, dividing the intensity in groups according to a magnitude of the intensity to subject the numbers to frequency calculating to obtain a histogram includes: equalizing the histogram with a L-shaped window:

$$n'_i = \sum_{i-L/2<=p<=i+L/2} n_p, 0 <= i <= N,$$

in which $n_p$ represents equalization of $n_i$, $n_i$ represents a sum of results of the equalization of $n_i$, and p represents an integer associated with the size of the L-shaped window and the $i^{st}$ line.

Figure 30:
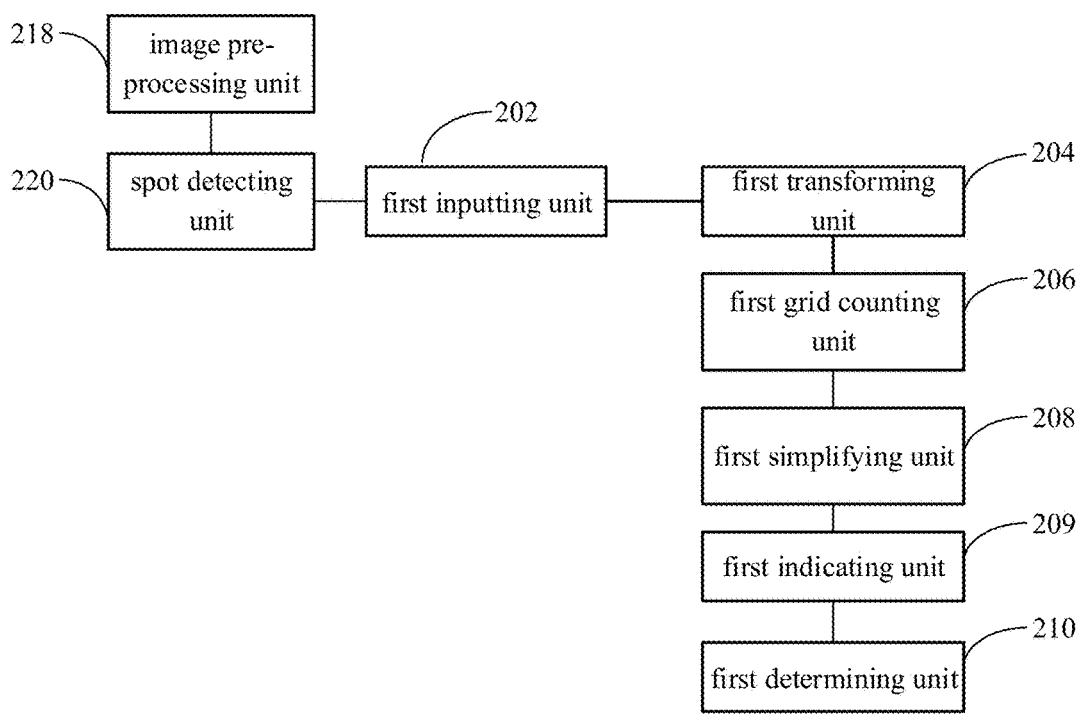
FIG. 30 is a block diagram of a device for identifying a single molecule according to an embodiment of the present disclosure.

In some embodiments, as shown in FIG. 30, the device 200 for identifying a single molecule also includes: an image pre-processing module 218, configured to analyze a to-be-processed image so as to obtain a first image, in which the to-be-processed image includes at least one spot having at least one pixel point; and a spot detecting module 220, configured to analyze the first image so as to compute a spot determining threshold; to analyze the first image so as to acquire a candidate spot; and to judge whether the candidate spot is the spot according to the spot determining threshold, acquiring the time sequence of the intensity of the spot if the candidate spot is the spot, and discarding the candidate spot if the candidate spot is not the spot.

Figure 31:
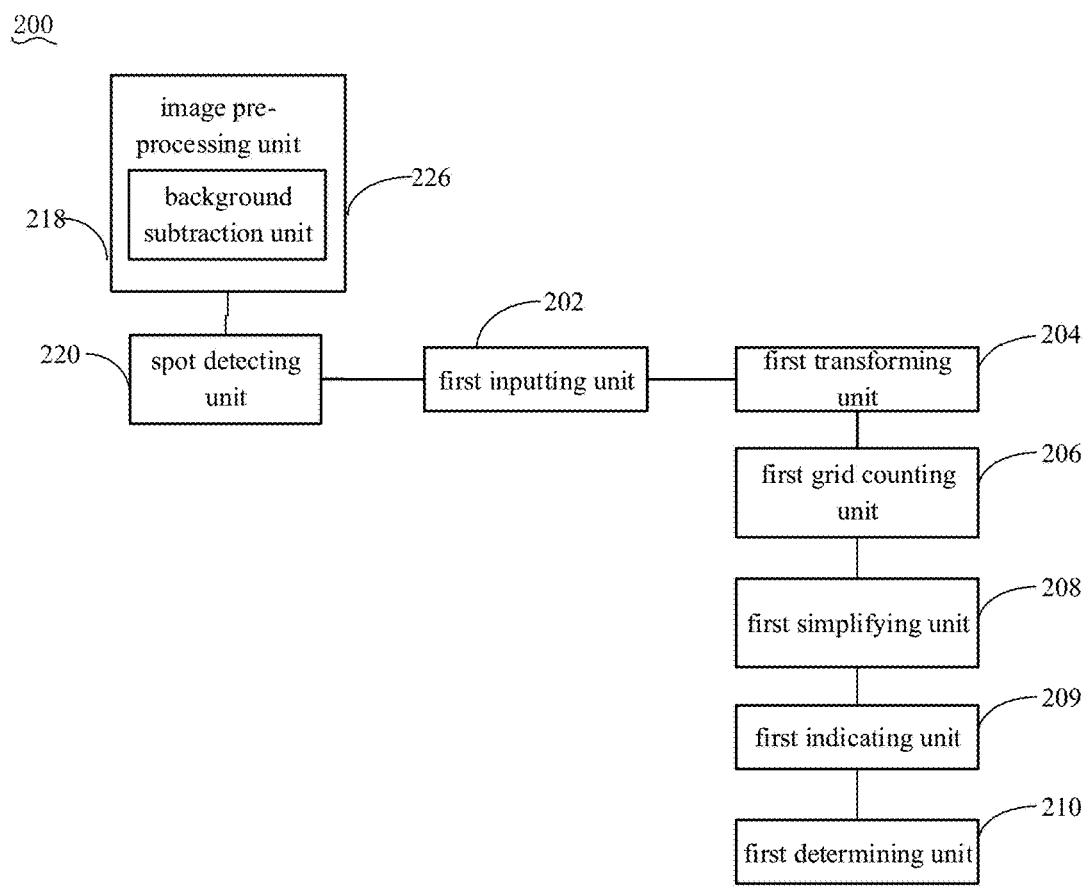
FIG. 31 is a block diagram of a device for identifying a single molecule according to an embodiment of the present disclosure.

In some implementations, referring to FIG. 31, the image pre-processing module 218 includes a background subtraction module 226. The background subtraction module 226 is configured to perform a background subtraction on the to-be-processed image so as to acquire the first image.

Figure 32:
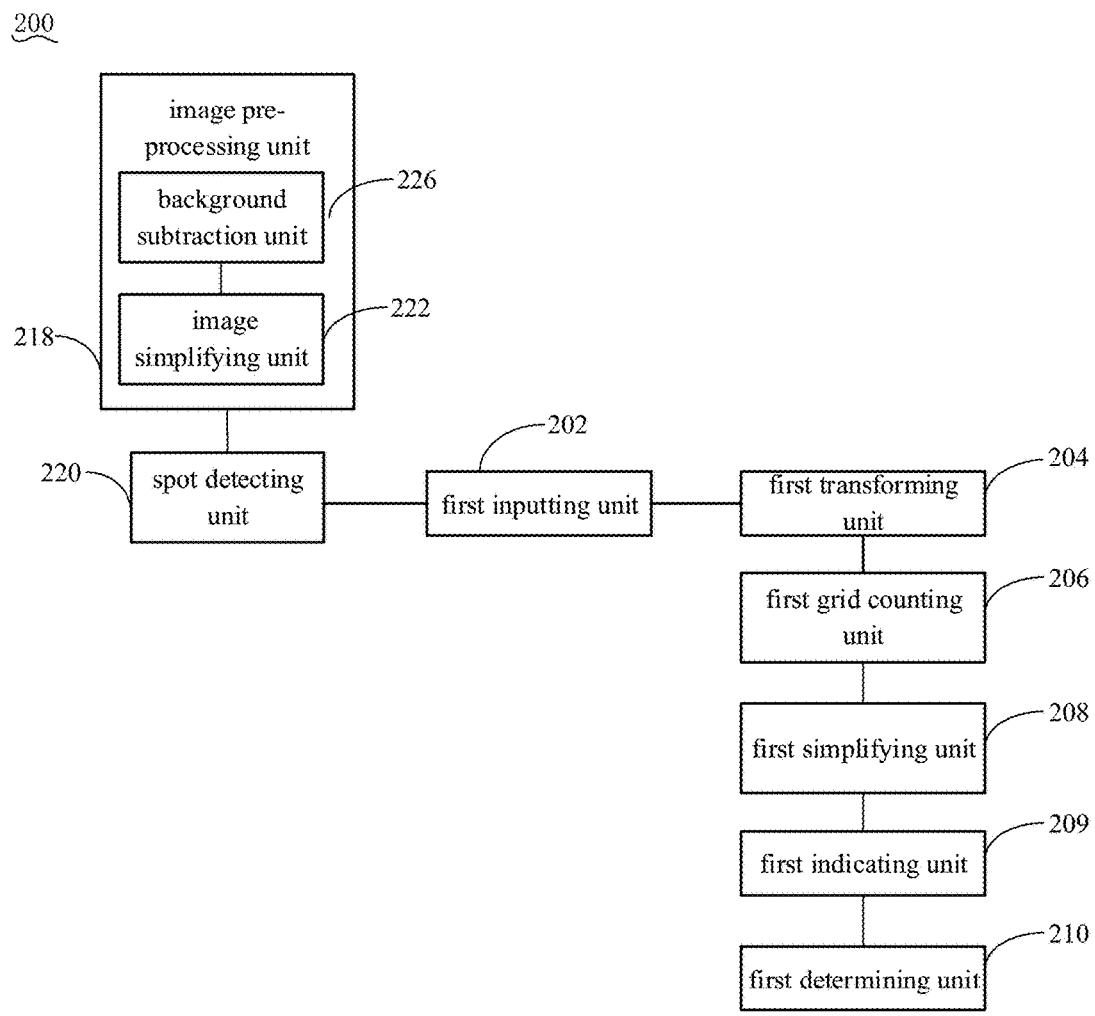
FIG. 32 is a block diagram of a device for identifying a single molecule according to an embodiment of the present disclosure.

In some implementations, referring to FIG. 32, the image pre-processing module 218 includes a simplifying module 222. The simplifying module 222 is configured to simplify the to-be-processed image after the background subtraction so as to acquire the first image.

Figure 33:
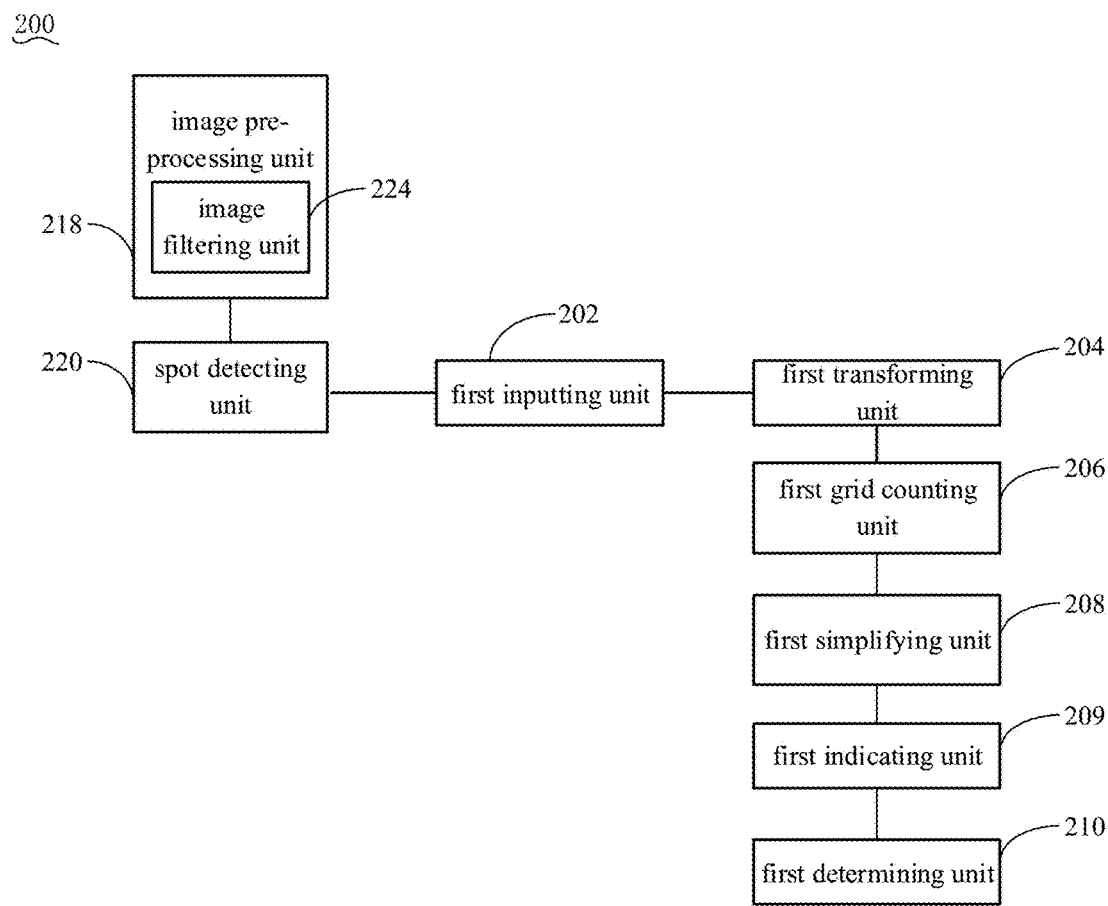
FIG. 33 is a block diagram of a device for identifying a single molecule according to an embodiment of the present disclosure.

In some implementations, referring to FIG. 33, the image pre-processing module 218 includes an image filtering module 224. The image filtering module 224 is configured to filter the to-be-processed image so as to acquire the first image.

Figure 34:
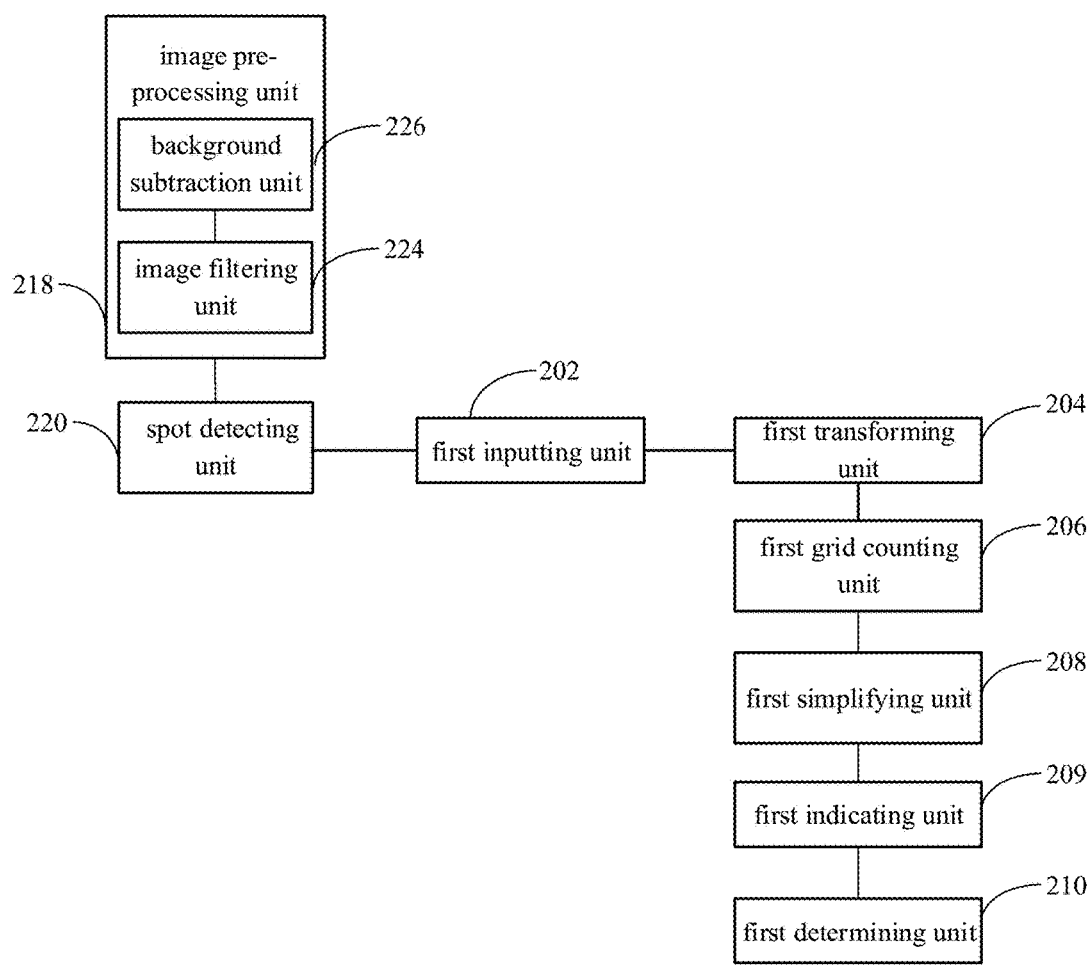
FIG. 34 is a block diagram of a device for identifying a single molecule according to an embodiment of the present disclosure.

In some implementations, referring to FIG. 34, the image pre-processing module 218 includes a background subtraction module 226 and an image filtering module 224. The background subtraction module 226 is configured to perform a background subtraction on the to-be-processed image, the image filtering module 224 is configured to filter the background subtracted image so as to acquire the first image.

Figure 35:
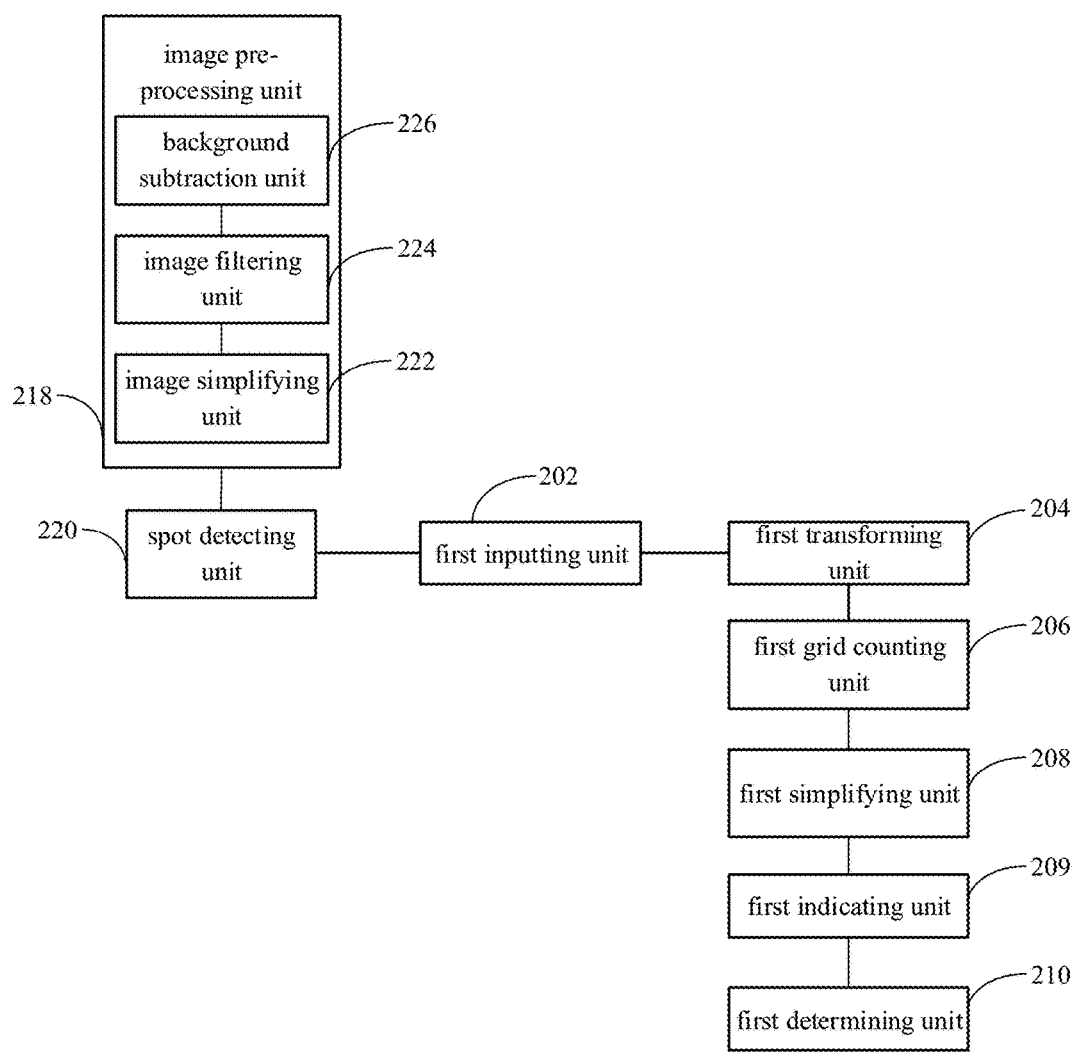
FIG. 35 is a block diagram of a device for identifying a single molecule according to an embodiment of the present disclosure.

In some implementations, referring to FIG. 35, the image pre-processing module 218 includes a simplifying module 222. The simplifying module 222 is configured to simplify the to-be-processed image after the background subtraction and the filtering so as to acquire the first image.

Figure 36:
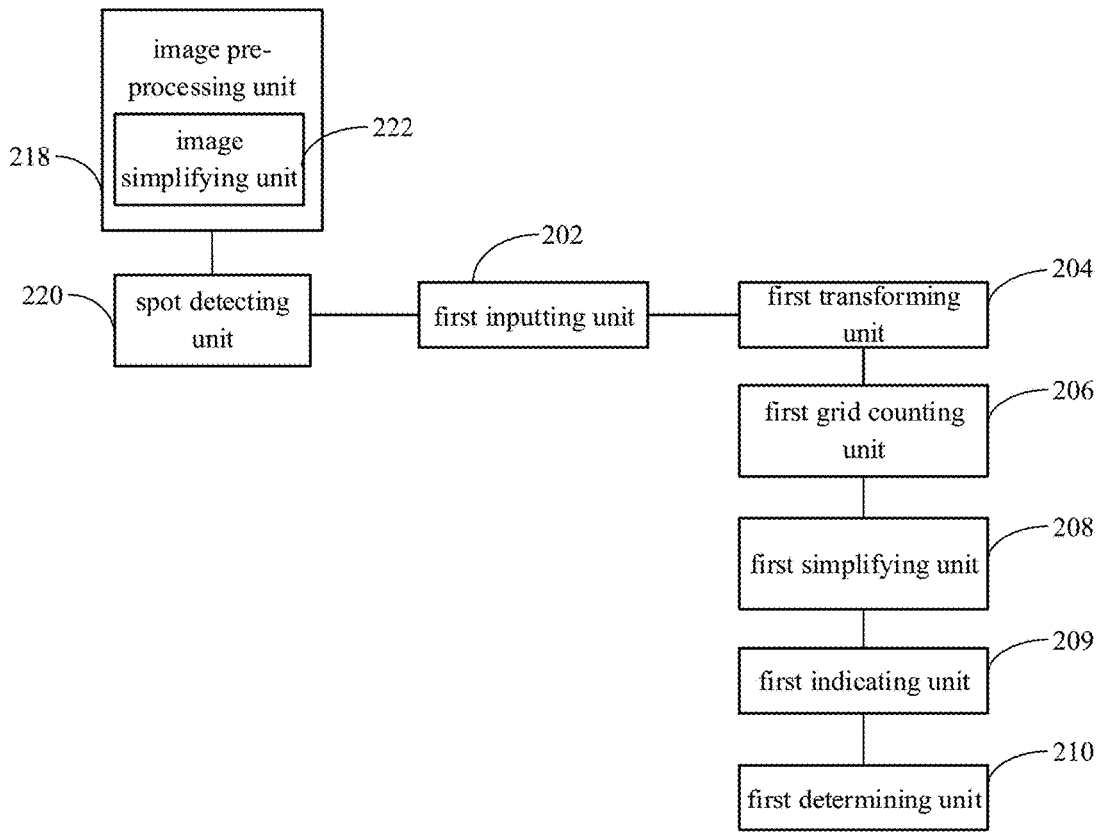
FIG. 36 is a block diagram of a device for identifying a single molecule according to an embodiment of the present disclosure.

In some implementations, referring to FIG. 36, the image pre-processing module 218 includes a simplifying module 222. The simplifying module 222 is configured to simplify the to-be-processed image so as to acquire the first image.

In some implementations, the background subtraction module 226 is configured to determine a background of the to-be-processed image by an opening operation; and to perform the background subtraction on the to-be-processed image according to the background.

In some implementations, the image filtering module 224 is configured to perform a Mexican Hat filtering on the to-be-processed image.

In some implementations, the simplifying module 222 is configured to perform a binary process.

Figure 37:
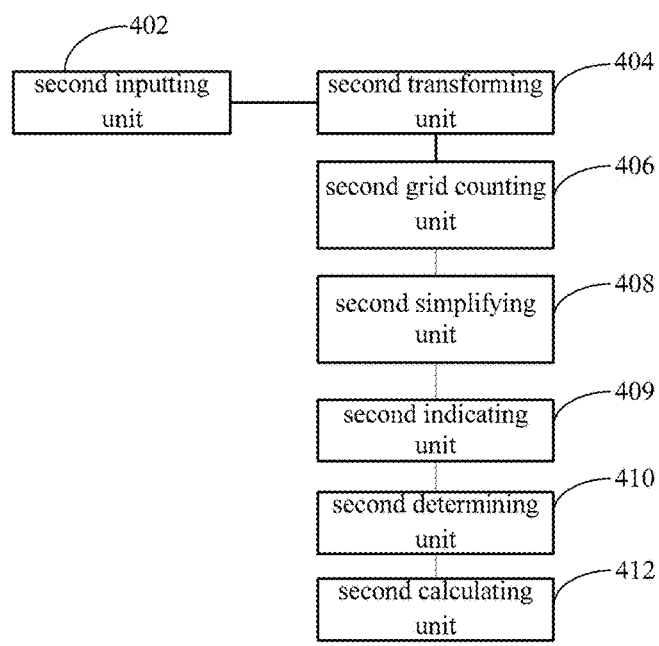
FIG. 37 is a block diagram of a device for counting a single molecule according to an embodiment of the present disclosure.

In some implementations, when using the simplifying module 222 to simplify the image, a signal-to-noise ratio matrix is acquired according to the to-be-processed image before the simplifying, and to simplify the to-be-processed image before the simplifying according to the signal-to-noise ratio matrix so as to acquire the first image. In some implementations, the spot detecting module 220 is configured to process the first image by an Otsu method so as to compute the spot determining threshold. In some implementations, the spot detecting module 220 is configured to: search in the first image for a pixel point with connectivity greater than (h*h−1) as a center of the candidate spot; and to judge whether the center of the candidate spot satisfies a condition of $I_{max}*A_{BI}*ceof_{guass}>T$, where $I_{max}$ is a maximum intensity of a center of the h*h window, $A_{BI}$ is a proportion of pixels in the first image being a set value in the h*h window, $ceof_{guass}$ is a correlation coefficient between a pixel in the h*h window and a two-dimensional Gaussion distribution, and T is the spot determining threshold, in which h is a natural number and particularly, an odd number greater than 1; to determine a spot corresponding to the center of the candidate spot as the spot when the condition is satisfied; and to discard the candidate spot when the condition fails to be satisfied. As shown in FIG. 37, a device 400 for counting a single molecule according to embodiments of the present disclosure is used to perform all of or part of the methods for counting the single molecule according to any embodiment or example described above. The device 400 for counting the single molecule includes: a second inputting unit 402 configured to input time sequence of an intensity of an spot; a second transforming unit 404 configured to form a line chart of time and intensity of the spot according to the time sequence of the second inputting unit 402, in which the line chart consists of a plurality of line segments; a second grid counting unit 406 configured to divide the line chart of the second transforming unit 404 into a plurality of grids in an array, and count the number of the line segments and/or ends of the line segments in each grid; a second simplifying unit 408 configured to subject the divided line chart to a line erosion according to numbers corresponding to the grids to transform the divided line chart to a simplified image; a second indicating unit 409 configured to subject the simplified image to run-length coding to indicate connected domains; a second determining unit 410 configured to calculate an area of each connected domain and determine that the connected domain corresponds to a single molecule if the area of the connected domain is greater than a first predetermined threshold; a second calculating unit 412 configured to obtain a first number of the single molecules by calculation. According to the device 400 for counting the single molecule, the line chart of the time sequence of the intensity of the spot is processed to transform into the image, thus obtaining the connected domains by run-length coding, which results in a quick count for the single molecule and a high accuracy of the count.

It should be noted that the description of the technical features and advantages of the method for counting the single molecule in any one of the above embodiments and examples is also applicable to the device 400 for counting the single molecule in embodiments of the present embodiment. In order to avoid redundancy, it is not further described in detail here.

Figure 38:
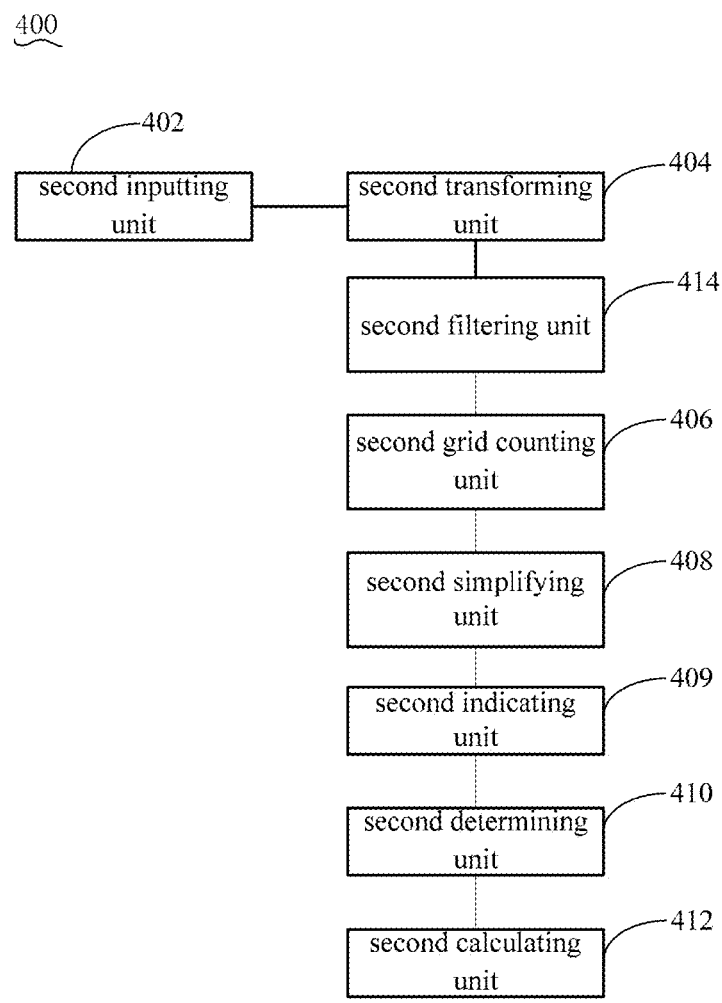
FIG. 38 is a block diagram of a device for counting a single molecule according to an embodiment of the present disclosure.

For example, in some embodiments, as shown in FIG. 38, the device 400 for counting the single molecule further includes a second filtering unit 414 connected to the second grid counting unit 406, configured to filter the line chart of the second transforming unit 404 before the line chart is divided in the plurality of grids in the array.

Figure 39:
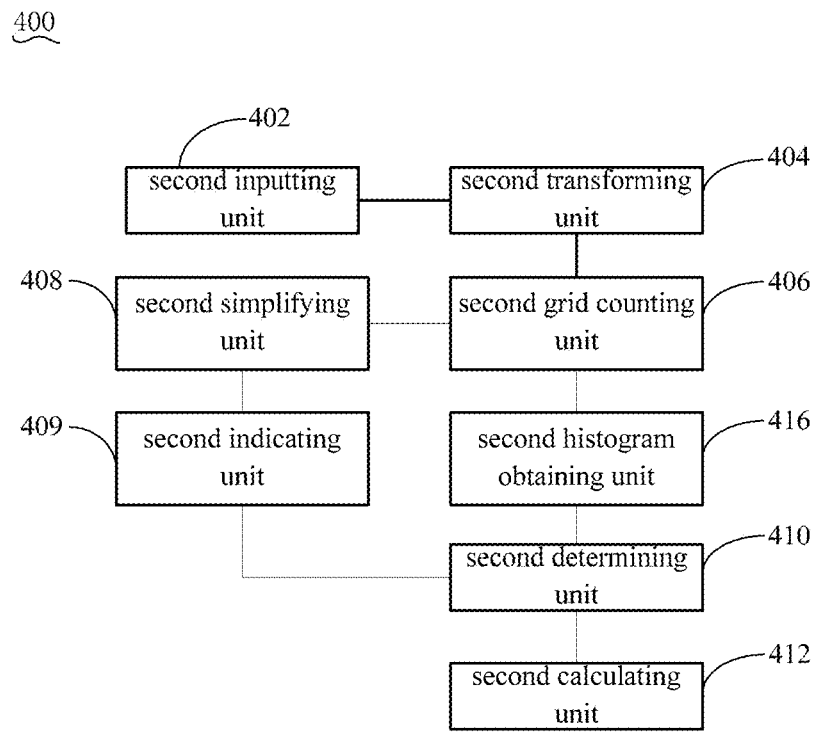
FIG. 39 is a block diagram of a device for counting a single molecule according to an embodiment of the present disclosure.

In some embodiments, as shown in FIG. 39, the device 400 for counting the single molecule further includes: a second histogram obtaining unit 416 configured to divide the intensity in groups according to a magnitude of the intensity to subject the numbers of the second grid counting unit 406 to frequency calculating to obtain a histogram, in which in the second determining unit 410, a maximum value of the histogram of the second histogram obtaining unit 416 is found and it is determined that a peak providing the maximum value corresponds to a single molecule if the maximum value is greater than a second predetermined threshold and the peak providing the maximum value has a width greater than a third predetermined threshold, and in the calculating unit 412, a second number of the single molecules is acquired by calculation and a small one of the first and second numbers is taken as a final number of the single molecules.

Figure 40:
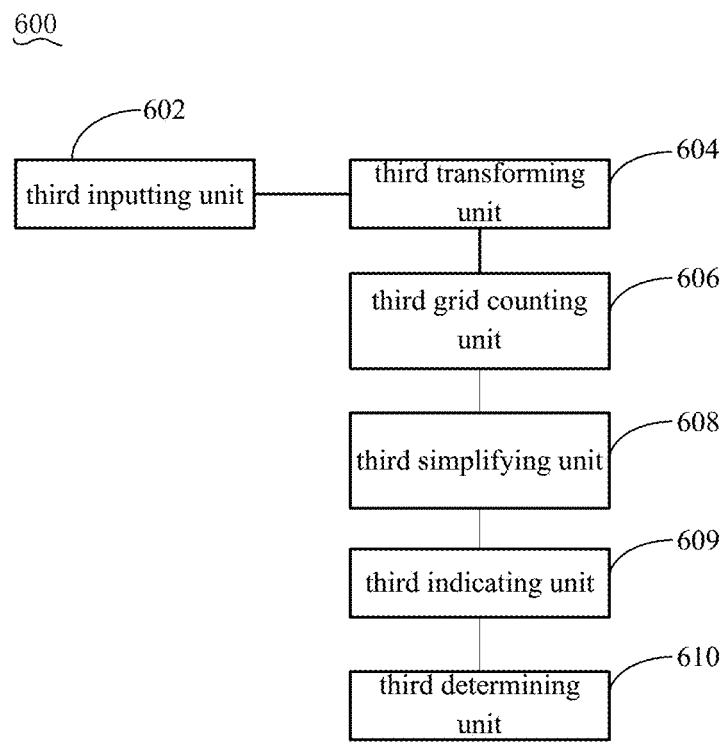
FIG. 40 is a block diagram of a device for counting a single molecule according to an embodiment of the present disclosure.

As shown in FIG. 40, a device 600 for counting a single molecule according to embodiments of the present disclosure includes: a third inputting unit 602 configured to input time sequence of an intensity of an spot; a third transforming unit 604 configured to form a line chart of time and intensity of the spot according to the time sequence of the third inputting unit 602, in which the line chart consists of a plurality of line segments; a third grid counting unit 606 configured to divide the line chart of the third transforming unit 604 into a plurality of grids in an array, and count the number of the line segments and/or ends of the line segments in each grid; a third simplifying unit 608 configured to subject the divided line chart to a line erosion according to numbers corresponding to the grids to transform the divided line chart to a simplified image; a third indicating unit 609 configured to subject the simplified image to run-length coding to indicate connected domains; a third determining unit 610 configured to calculate an area of each connected domain and determine that 1 is added to the number of the single molecule if the area of the connected domain is greater than a first predetermined threshold.

According to the device 600 for counting the single molecule, the line chart of the time sequence of the intensity of the spot is processed to transform into the image, thus obtaining the connected domains by run-length coding, which results in a quick count for the single molecule and a high accuracy of the count.

It should be noted that the description of the technical features and advantages of the method for counting the single molecule in any one of the above embodiments and examples is also applicable to the device 600 for counting the single molecule in embodiments of the present embodiment. In order to avoid redundancy, it is not further described in detail here.

Figure 41:
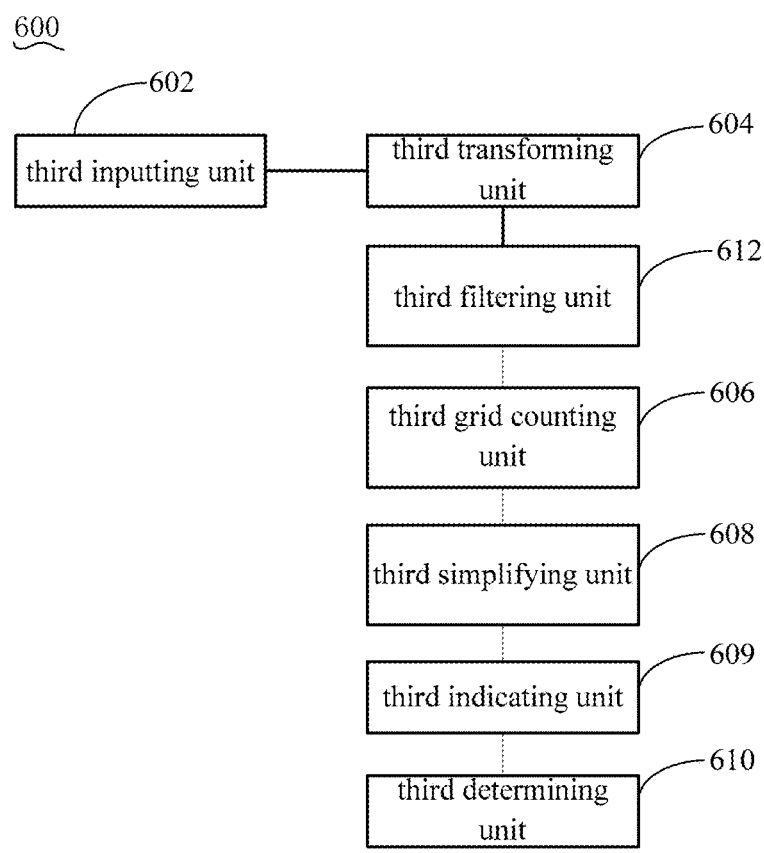
FIG. 41 is a block diagram of a device for counting a single molecule according to an embodiment of the present disclosure.

For example, in some embodiments, as shown in FIG. 41, the device 600 for counting the single molecule further includes a third filtering unit 612 connected to the third grid counting unit 606, configured to filter the line chart of the third transforming unit 604 before the line chart is divided in the plurality of grids in the array.

Figure 42:
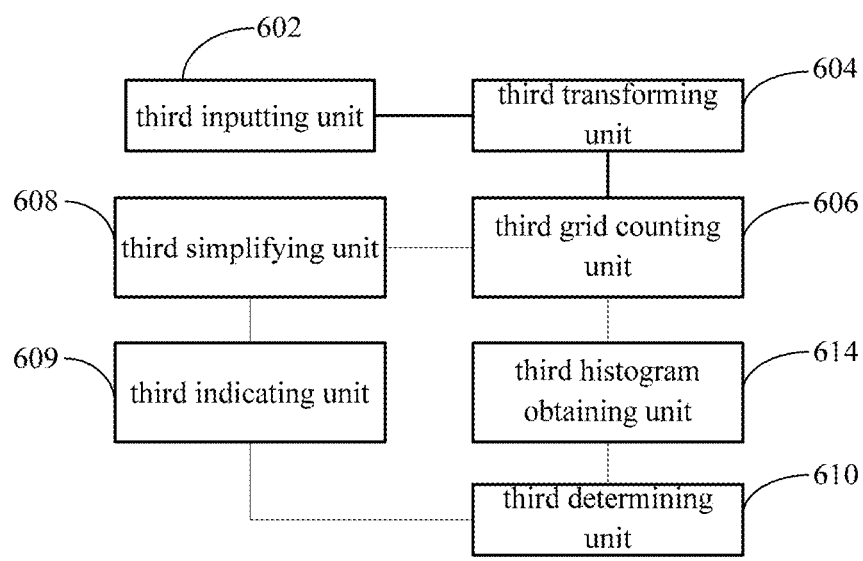
FIG. 42 is a block diagram of a device for counting a single molecule according to an embodiment of the present disclosure.

In some embodiments, as shown in FIG. 42, the device 600 for counting the single molecules further includes: a third histogram obtaining unit 614 configured to divide the intensity in groups according to a magnitude of the intensity to subject the numbers from the third grid counting unit 606 to frequency calculating to obtain a histogram, in which in the third determining unit 610, a maximum value of the histogram from the third histogram obtaining unit 614 is found and it is determined that 1 is added to the number of the single molecule if the maximum value is greater than a second predetermined threshold and the peak providing the maximum value has a width greater than a third predetermined threshold, the number of the single molecules obtained from the histogram is compared to the number of the single molecules obtained from the run-length coding, and a small one of the two numbers is taken as a final number of the single molecules.

Figure 43:
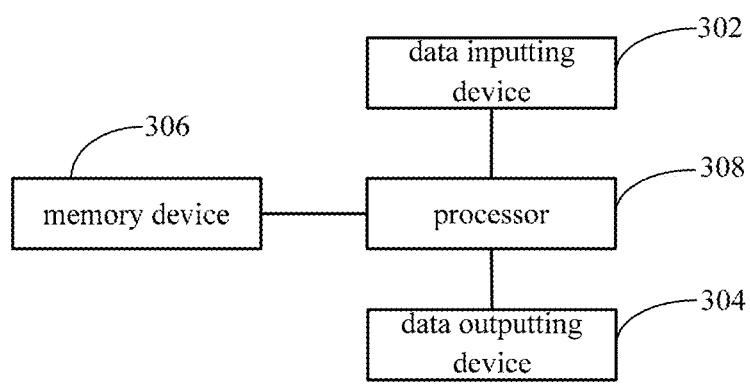
FIG. 43 is a block diagram of a system for processing a single molecule according to an embodiment of the present disclosure.

As shown in FIG. 43, a system 300 for processing a single molecule according to embodiments of the present disclosure includes: a data inputting device 302 configured to input data; a data outputting device 304 configured to output data; a memory device 306 configured to store data including a computer executable program; and a processor 308 configured to perform the computer executable program for performing a method for identifying a single molecule or a method for counting a single molecule according to any embodiment described above.

A computer readable memory medium according to embodiments of the present disclosure is configured to store a program that, when executed by a computer, causes the computer to perform any method described above. The computer readable memory medium may be a read-only memory, a random access memory, a magnetic disc, an optical disc, etc.

Reference throughout this specification to "one embodiment", "some embodiments," "an embodiment," "a specific example," or "some examples," means that a particular feature, structure, material, or characteristic described in connection with the embodiment or example is included in at least one embodiment or example of the present disclosure. Thus, the appearances of the phrases in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated that the above embodiments are explanatory and cannot be construed to limit the present disclosure, and changes, alternatives, and modifications can be made in the embodiments without departing from scope of the present disclosure by those skilled in the art.

What is claimed is:

1. A method for identifying a single molecule, comprising:
    (a) inputting time sequence of an intensity of a spot;
    (b) forming a line chart of time and intensity of the spot according to the time sequence, wherein the line chart consists of a plurality of line segments;
    (c) dividing the line chart into a plurality of grids in an array and counting the number of the line segments and/or ends of the line segments in each grid;
    (d) subjecting the divided line chart to a line erosion according to numbers corresponding to the grids to transform the divided line chart to a simplified image;
    (e) subjecting the simplified image to run-length coding to indicate connected domains; and
    (f) calculating an area of each connected domain and determining that a connected domain corresponds to a single molecule if the area of the connected domain is greater than a first predetermined threshold.

2. The method according to claim 1, further comprising:
    obtaining a first number of single molecules by calculation.

3. The method according to claim 2, further comprising:
    dividing the intensity in groups according to a magnitude of the intensity to subject the numbers to frequency calculating to obtain a histogram;
    finding a maximum value of the histogram and determining that a peak providing the maximum value corresponds to a single molecule if the maximum value is greater than a second predetermined threshold and the peak providing the maximum value has a width greater than a third predetermined threshold; and
    obtaining a second number of the single molecules by calculation and taking a small one of the first and second numbers as a final number of the single molecules.

4. The method according to claim 1, wherein in step (f), 1 is added to a number of the single molecules if the area of the connected domain is greater than a first predetermined threshold.

5. The method according to claim 4, further comprising:
dividing the intensity in groups according to a magnitude of the intensity to subject the numbers to frequency calculating to obtain a histogram;
finding a maximum value of the histogram and determining that 1 is added to the number of the single molecule if the maximum value is greater than a second predetermined threshold and the peak providing the maximum value has a width greater than a third predetermined threshold; and
comparing the number of the single molecules obtained from the histogram to the number of the single molecules obtained from the run-length coding and taking a small one of the two numbers as a final number of the single molecules.

6. The method according to claim 1, further comprising:
dividing the intensity in groups according to a magnitude of the intensity to subject the numbers to frequency calculating to obtain a histogram; and
finding a maximum value of the histogram and determining that a peak providing the maximum value corresponds to a single molecule if the maximum value is greater than a second predetermined threshold and the peak providing the maximum value has a width greater than a third predetermined threshold.

7. The method according to claim 6, wherein dividing the intensity in groups according to the magnitude of the intensity to subject the numbers to frequency calculating to obtain the histogram comprises:
dividing the intensity in N groups according to the magnitude of the intensity and calculating frequencies of the numbers in the N groups:

$$n_i = \sum_{0<=j<=M} g_{i,j}, 0 <= i <= N$$

wherein $n_i$ represents a sum of the frequencies of the numbers of an $i^{st}$ line of the grids, j represents a time frame, $g_{ij}$ represents a frequency of the number of grid (i,j), and M represents the number of the time frames.

8. The method according to claim 7, wherein dividing the intensity in groups according to the magnitude of the intensity to subject the numbers to frequency calculating to obtain the histogram comprises:
equalizing the histogram with a L-shaped window:

$$n'_i = \sum_{i-L/2<=p<=i+L/2} n_p, 0 <= i <= N$$

wherein $n_p$ represents equalization of $n_i$, $n_i$ represents a sum of results of the equalization of $n_i$, and p represents an integer associated with the size of the L-shaped window and the $i^{st}$ line.

9. The method according to claim 1, wherein before dividing the line chart into the plurality of grids in the array, the method further comprises filtering the line chart.

10. The method according to claim 1, wherein the line chart is divided into the plurality of grids in the array according to a time frame of the intensity when collected and a magnitude of the intensity.

11. The method according to claim 1, further comprising:
an image pre-processing step comprising: analyzing a to-be-processed image so as to obtain a first image, wherein the to-be-processed image comprises at least one spot having at least one pixel point; and
a spot detecting step comprising:
analyzing the first image so as to compute a spot determining threshold;
analyzing the first image so as to acquire a candidate spot; and
determining whether the candidate spot is the spot according to the spot determining threshold,
acquiring the time sequence of the intensity of the spot if the candidate spot is the spot, and
discarding the candidate spot if the candidate spot is not the spot.

12. The method according to claim 11, wherein the image pre-processing step further comprises performing a background subtraction on the to-be-processed image so as to acquire the first image.

13. The method according to claim 12, wherein the image pre-processing step further comprises performing a simplifying on the to-be-processed image after the background subtraction so as to acquire the first image.

14. The method according to claim 11, wherein the image pre-processing step further comprises performing a filtering on the to-be-processed image so as to acquire the first image.

15. The method according to claim 11, wherein the image pre-processing step further comprises performing a simplifying on the to-be-processed image, which has been subjected to the background subtraction and then a filtering, so as to acquire the first image.

16. The method according to claim 11, wherein the image pre-processing step further comprises performing a simplifying on the to-be-processed image so as to acquire the first image.

17. The method according to claim 16, wherein performing the simplifying comprises:
acquiring a signal-to-noise ratio matrix according to the to-be-processed image before the simplifying, and
simplifying the to-be-processed image according to the signal-to-noise ratio matrix so as to acquire the first image.

18. The method according to claim 16, wherein determining whether the candidate spot is the spot according to the spot determining threshold comprises:
searching in the first image for a pixel point with connectivity greater than (h*h−1) as a center of the candidate spot, wherein h is an odd number greater than 1; and
determining whether the center of the candidate spot satisfies a condition of $I_{max}*A_{BI}*ceof_{guass}>T$, where $I_{max}$ is a maximum intensity of a center of the h*h window, $A_{BI}$ is a proportion of pixels in the first image being a set value in the h*h window, $ceof_{guass}$ is a correlation coefficient between a pixel in the h*h window and a two-dimensional Gaussian distribution, and T is the spot determining threshold;
determining the candidate spot as the spot if the condition is satisfied; and
discarding the candidate spot if the condition fails to be satisfied.

19. A system for processing a single molecule, comprising:
a data inputting device configured to input data;
a data outputting device configured to output data;

a memory device configured to store data comprising a computer executable program configured to perform the method for identifying a single molecule according to claim 1; and a processor configured to perform the computer executable program.

20. The method of claim 1, wherein the inputting the time sequence of the intensity of the spot comprises:

irradiating a sample that comprises the single molecule with a laser beam of a wavelength; and collecting an image comprising the spot, which corresponds to fluorescence emitted by the sample.

* * * * *